US011332515B2

(12) United States Patent
Kakkar et al.

(10) Patent No.: US 11,332,515 B2
(45) Date of Patent: May 17, 2022

(54) MULTI-EPITOPIC CONSTRUCT

(71) Applicants: THROMBOSIS RESEARCH INSTITUTE, London (GB); Lord Kakkar, London (GB)

(72) Inventors: Vijay Kakkar, London (GB); Xinjie Lu, London (GB)

(73) Assignee: THROMBOSIS RESEARCH INSTITUTE, London (GB)

(*) Notice: Subject to any disclaimer, the term of this patent is extended or adjusted under 35 U.S.C. 154(b) by 60 days.

(21) Appl. No.: 15/546,858

(22) PCT Filed: Jan. 25, 2016

(86) PCT No.: PCT/GB2016/050150
§ 371 (c)(1),
(2) Date: Jul. 27, 2017

(87) PCT Pub. No.: WO2016/120596
PCT Pub. Date: Aug. 4, 2016

(65) Prior Publication Data
US 2018/0273608 A1    Sep. 27, 2018

(30) Foreign Application Priority Data
Jan. 27, 2015 (GB) .................................. 1501354
Jun. 11, 2015 (GB) .................................. 1510195

(51) Int. Cl.
| | |
|---|---|
| C07K 14/775 | (2006.01) |
| A61K 39/00 | (2006.01) |
| A61K 39/118 | (2006.01) |
| C07K 14/195 | (2006.01) |
| C07K 14/35 | (2006.01) |
| C07K 14/295 | (2006.01) |
| C07K 14/47 | (2006.01) |
| C07K 14/705 | (2006.01) |

(52) U.S. Cl.
CPC ........ *C07K 14/775* (2013.01); *A61K 39/0005* (2013.01); *A61K 39/0008* (2013.01); *A61K 39/0012* (2013.01); *A61K 39/118* (2013.01); *C07K 14/195* (2013.01); *C07K 14/295* (2013.01); *C07K 14/35* (2013.01); *C07K 14/47* (2013.01); *C07K 14/70596* (2013.01); *A61K 2039/58* (2013.01); *A61K 2039/6081* (2013.01); *A61K 2039/64* (2013.01)

(58) Field of Classification Search
None
See application file for complete search history.

(56) References Cited

U.S. PATENT DOCUMENTS 8,435,538 B2 * 5/2013 Kakkar .................... A61P 9/10
424/192.1
2011/0045012 A1    2/2011 Kakkar et al.

FOREIGN PATENT DOCUMENTS

| GB | 2539743 A | 12/2016 |
| GB | 2539743 A8 | 12/2016 |
| WO | 200157210 A2 | 8/2001 |
| WO | 200194411 A1 | 12/2001 |
| WO | 2009125231 A2 | 10/2009 |
| WO | 2013156771 A1 | 10/2013 |

OTHER PUBLICATIONS

Arteriosclerosis: https://meshb.nlm.nih.gov/record/ui?name=ARTERIOSCLEROSIS retrieved Jun. 19, 2019.*
Atherosclerosis: https://meshb.nlm.nih.gov/record/ui?ui=D050197 retrieved Jun. 19, 2019.*
Atheroma: https://meshb.nlm.nih.gov/record/ui?ui=D058226 retrieved Jun. 19, 2019.*
Mery et al. JBC 269:3457-3463, 1994.*
Xia et al. PloS ONE 10(4):e0123393, 29 pages Apr. 1, 2015.*
Ait-Oufella et al., Natural regulatory T cells control the development of atherosclerosis in mice; Nature Medicine; 2006, vol. 12, No. 2, 3-pages.
Fontenot et al., Foxp3 programs the development and function of CD4+CD25+ regulatory T cells; Nature Immunology; 2003; vol. 4, No. 4, 7-pages.
Hori et al., Control of Regulatory T Cell Development by the Transcription Factor Foxp3; Science; 2003; vol. 299, 6-pages.
Mor et al., Role of Naturally Occurring CD4+CD25+ Regulatory T Cells in Experimental Atherosclerosis; Arterioscler Throm Vase Biol., 8-pages.
Chintala et al., SCH 602539, a Protease-Activated Receptor-1 Antagonist, Inhibits Thrombosis Alone and in Combination With Cangrelor in a Folts Model of Arterial Thrombosis in Cynomolgus Monkeys, Integrative Physiology and Experimental Medicine 13 pages. Arterioscler Thromb Vasc Biol 2010;30:2143-2149.
Li et al., ApoB-100 and HSP60 Peptides Exert a Synergetic Role in Inhibiting Early Atherosclerosis in Immunized ApoE-null Mice, Protein & Peptide Letters, 2011, vol. 18, pp. 733-740.
Lu et al., Impact of multiple antigentic epitopes from ApoB100, hHSP60 and Chlamydophila pneumoniae on atherosclerotic lesion development in Apobtm2SgyLdlrtm1Her J Mice; Atherosclerosis, vol. 225, 2012, pp. 56-68.

(Continued)

*Primary Examiner* — Oluwatosin A Ogunbiyi
(74) *Attorney, Agent, or Firm* — Stinson LLP

(57) ABSTRACT

The invention relates to multiple epitope constructs, immunogenic and vaccine compositions comprising recombinant molecules presenting inserted multiple and different epitopes from a variety of antigens. The antigenic determinants being associated with different pathways leading to atherosclerosis. In particular, the invention relates to such compositions for eliciting an immune response against antigens and pathogens involved in the development of atherosclerosis the invention includes inter *alia* methods of treating and/or preventing the disease and recombinant protein products.

16 Claims, 26 Drawing Sheets

Specification includes a Sequence Listing.

(56) References Cited

OTHER PUBLICATIONS

Lu et al., Immunization With a Combination of 2 Peptides Derived From the C5a Receptor Significantly Reduces Early Atherosclerotic Lesion in Apobtm2SgyLdlrtm1Her J Mice; Integrative Physiology/Experimental Medicine, 29 pages. Aterioscler Thromb Vase Biol Including supplement pp. 1-16 32:2358-2371 2012.

Mundkur et al., Oral dosing with multi-antigenic construct induces atheroprotective immune tolerance to individual peptides in mice, International Journal of Cardiology, vol. 175, 2014, pp. 340-351.

Lu et al., Immunization With A Combination of 2 Peptides Derived From The C5a Receptor Significantly Reduces Early Atherosclerotic Lesion in Ldlrtm1her Apobtm2Sgy J Mice; 14-pages. Arterioscler Thromb Vase Biol 32:2358;2371 2012.

* cited by examiner

Fig. 1A
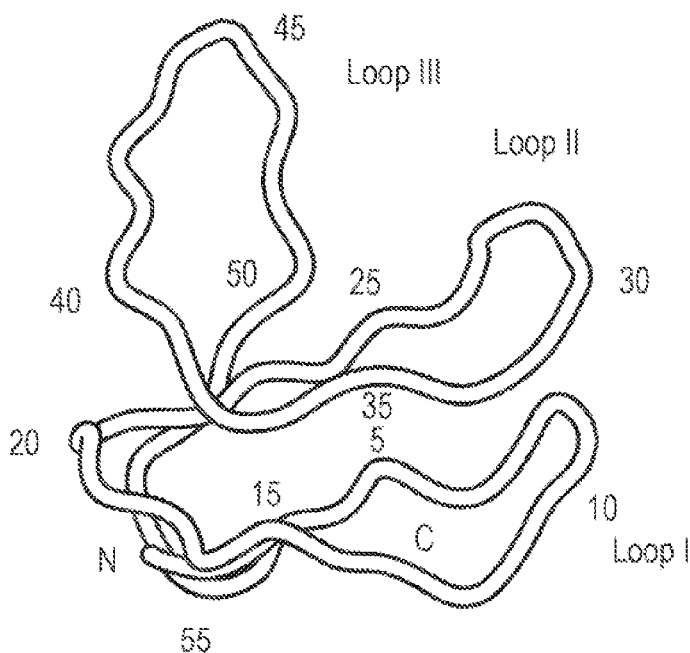
Fig. 1B
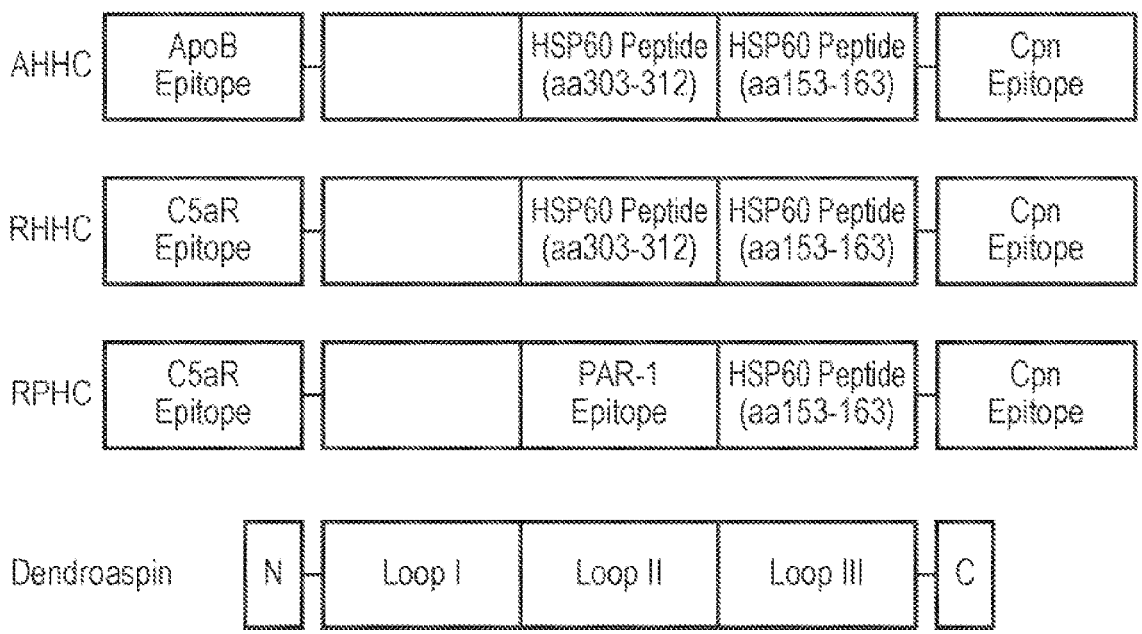
Figs. 1A - 1B

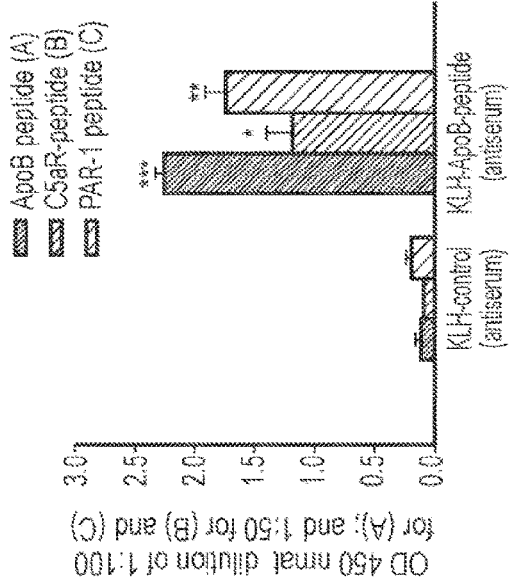
Fig. 2F
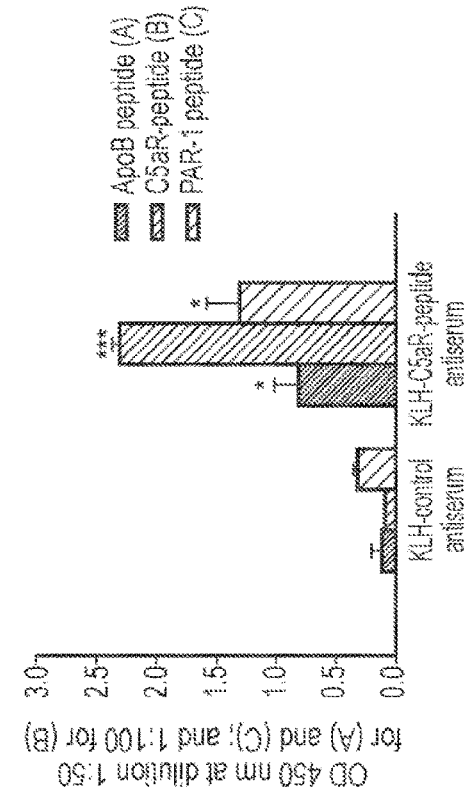
Fig. 2G
Fig. 2E - 2G
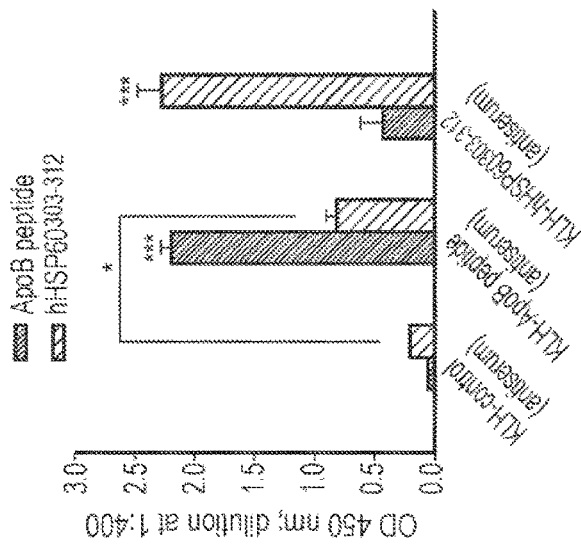
Fig. 2E

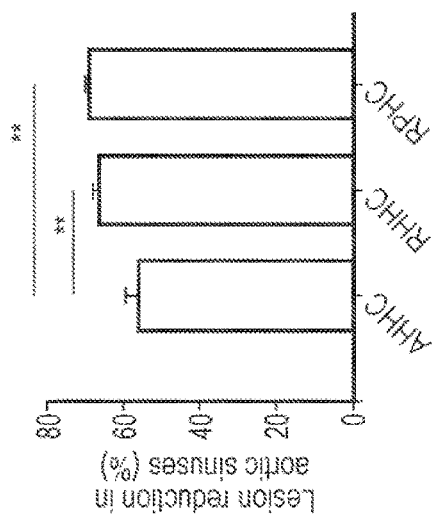
Fig. 3C
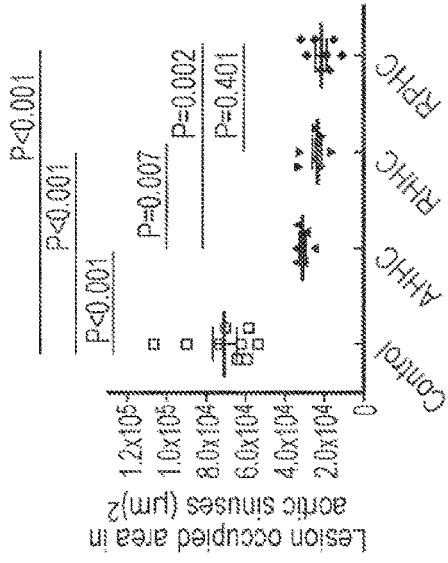
Fig. 3B
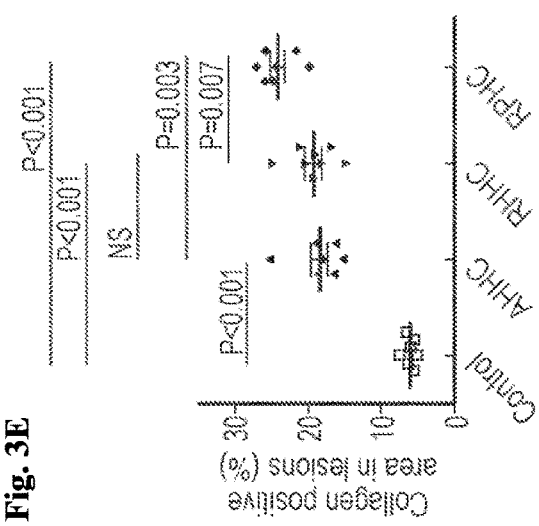
Fig. 3E
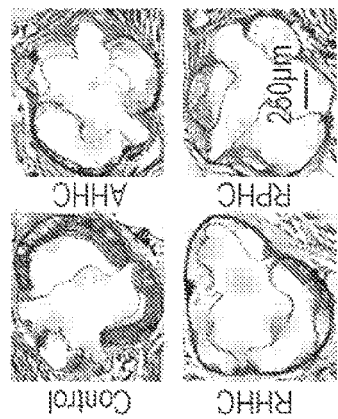
Fig. 3A
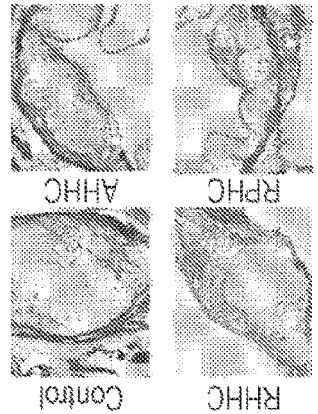
Fig. 3D
Fig. 3A - 3E

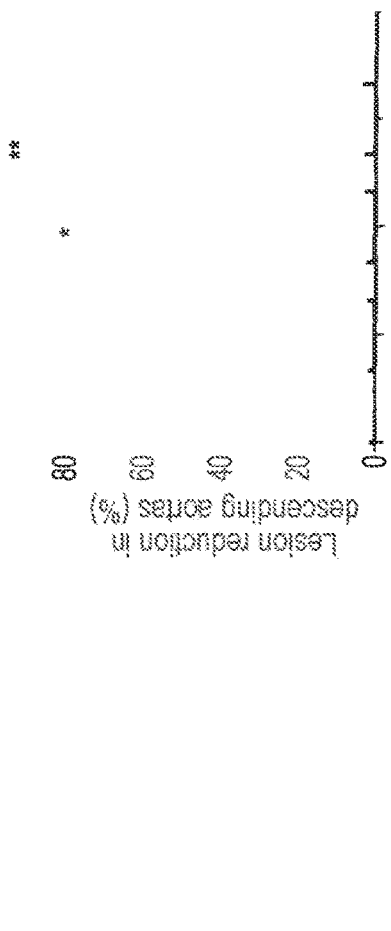
Fig. 3F
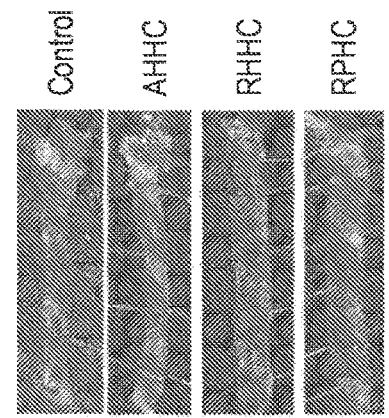
Fig. 3H
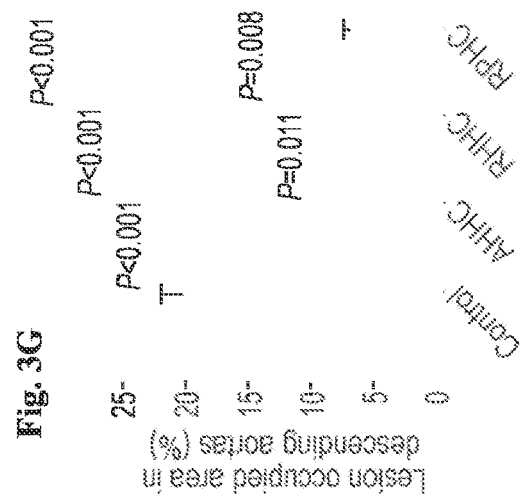
Fig. 3G
Figs. 3F - 3H

Fig. 4A
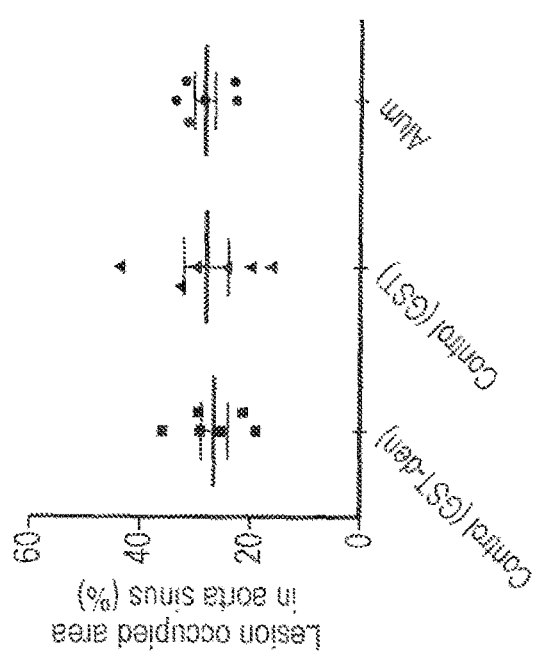
Fig. 4B
Fig. 4A – 4B

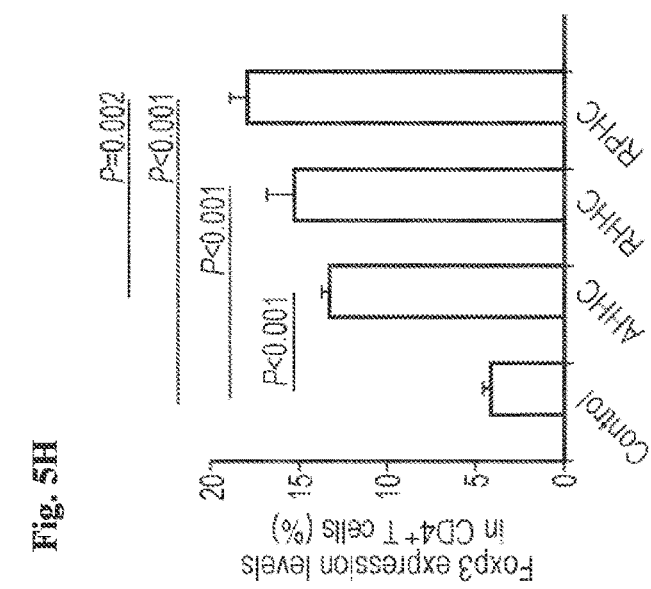
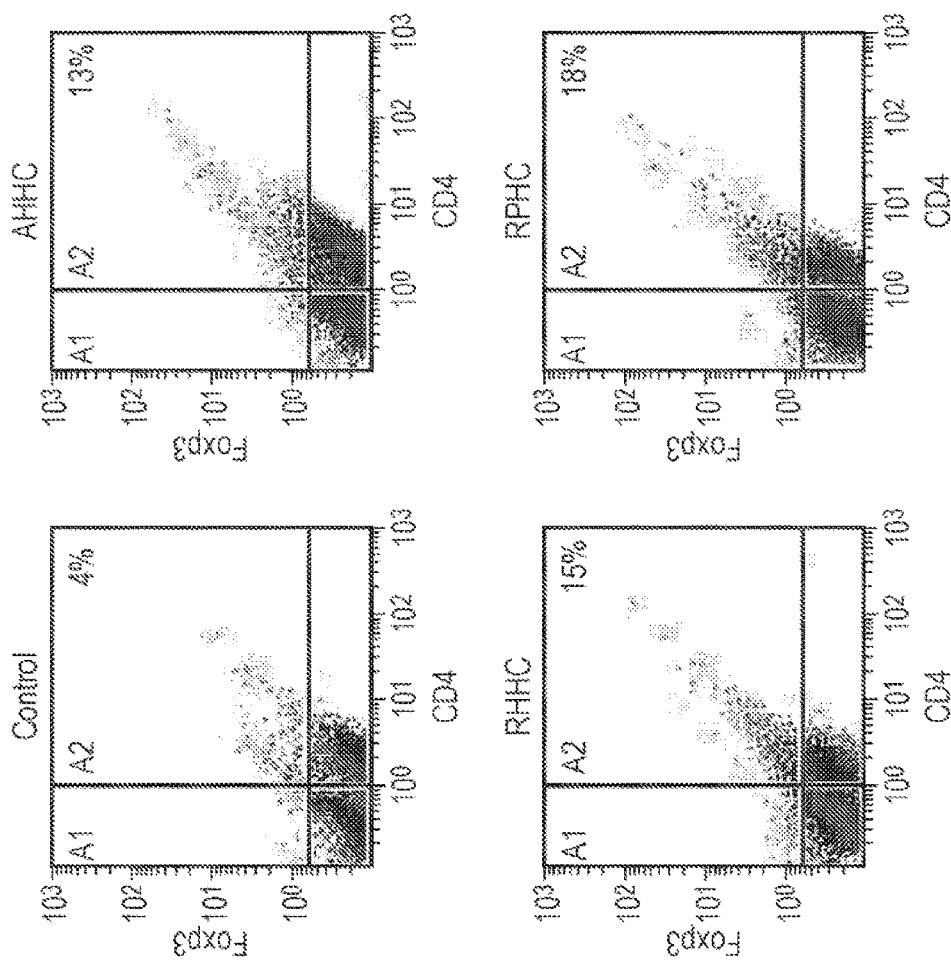
Fig. 5G
Figs. 5G - 5H

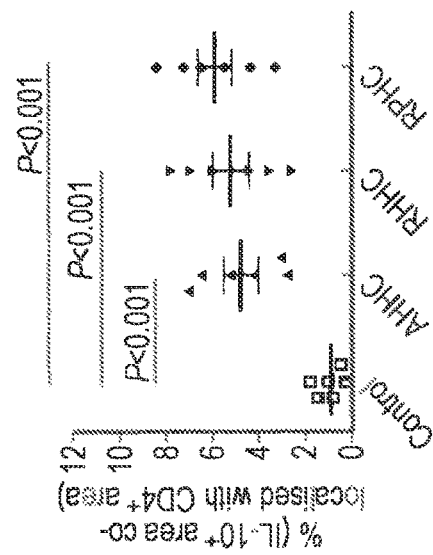
Fig. 6A
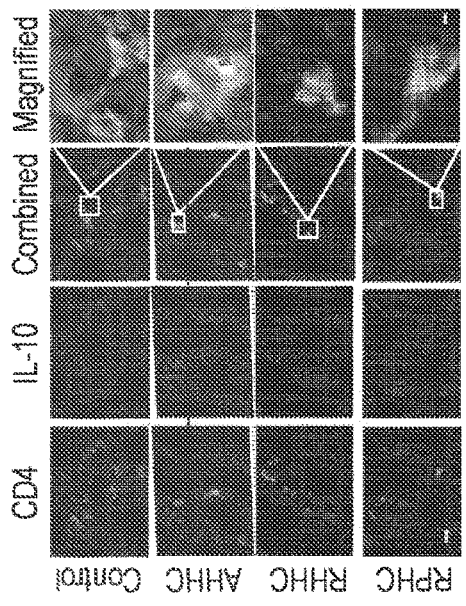
Fig. 6B
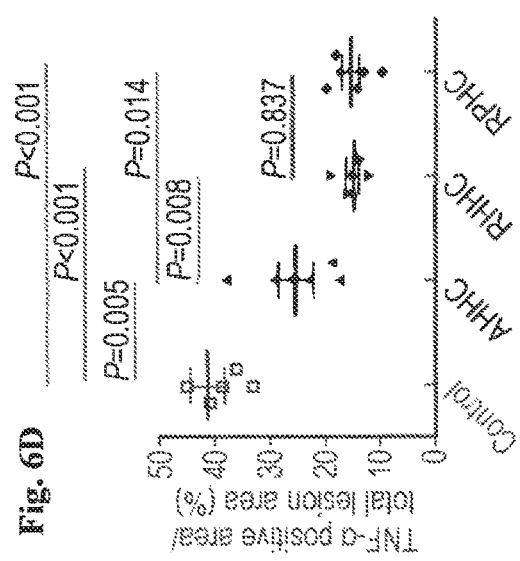
Fig. 6C
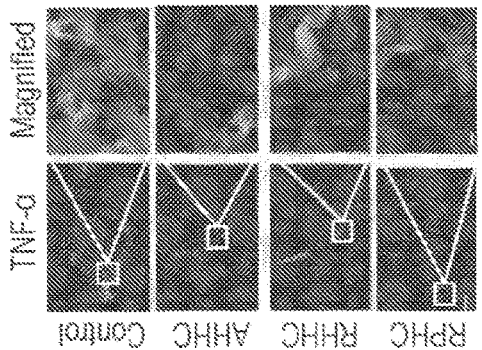
Fig. 6D
Figs. 6A - 6D

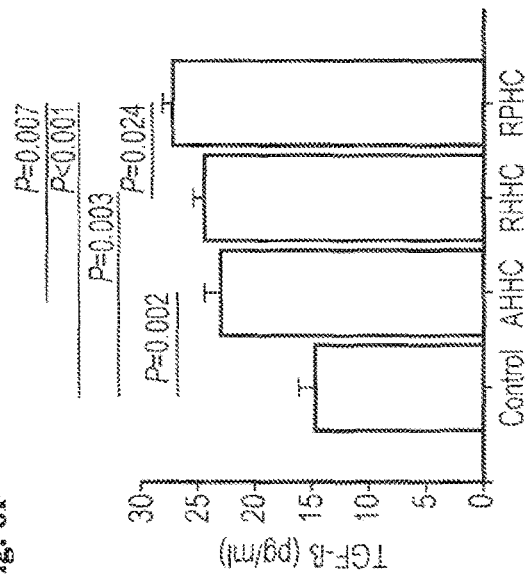
Fig. 6E
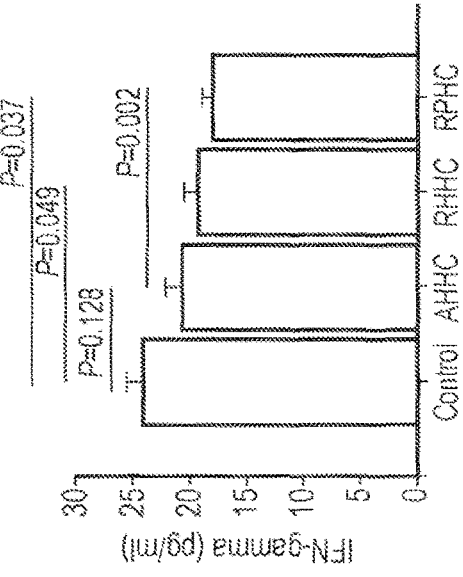
Fig. 6F
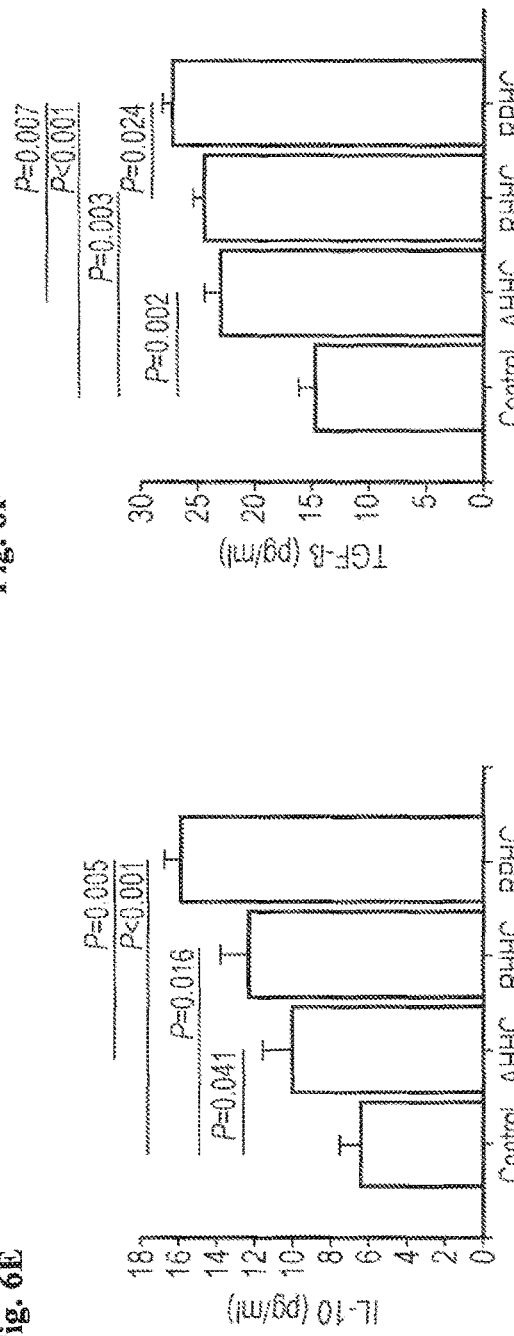
Fig. 6G
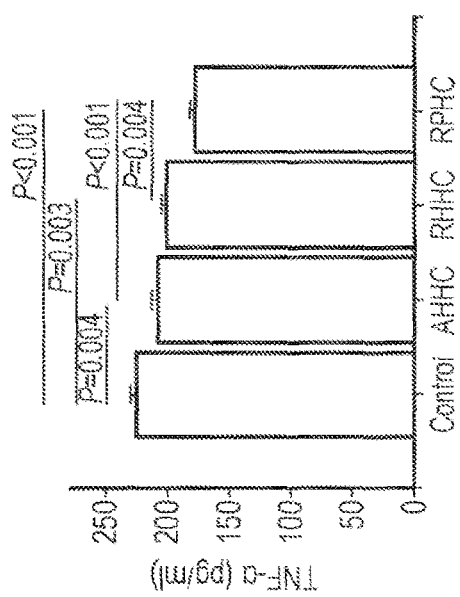
Fig. 6H
Figs. 6E - 6H

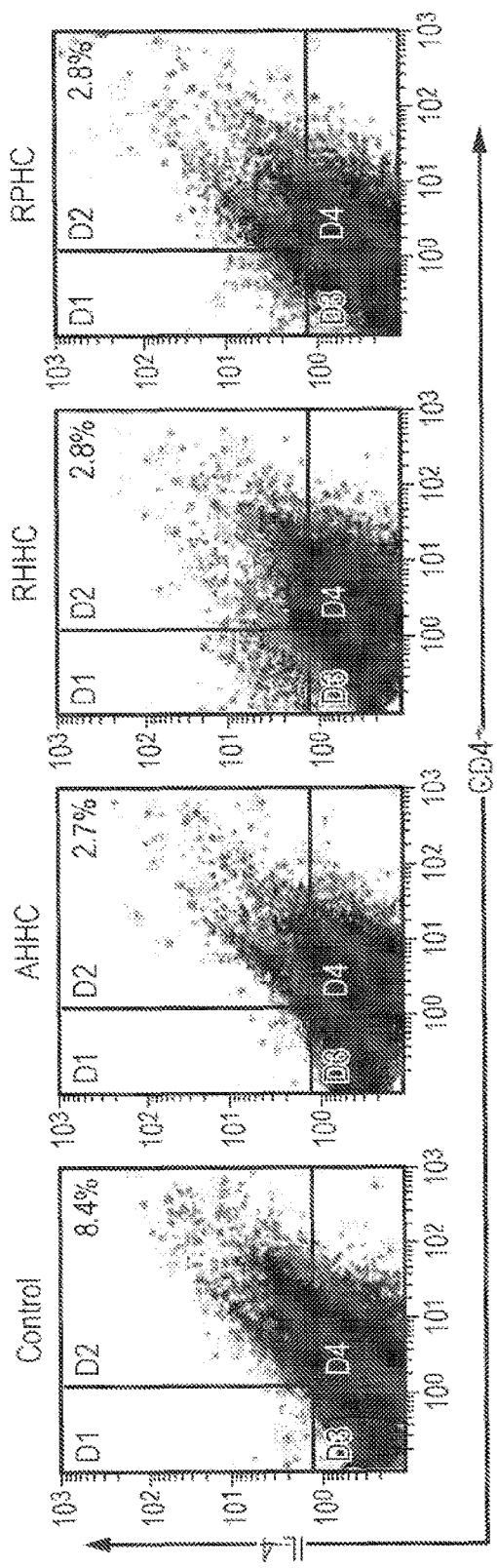
Fig. 6M
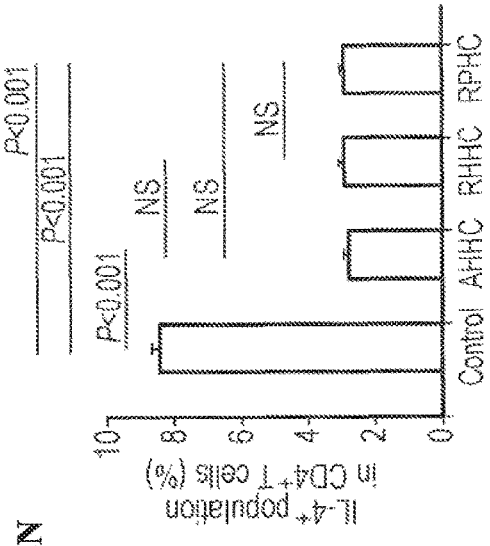
Fig. 6N
Figs. 6M - 6N

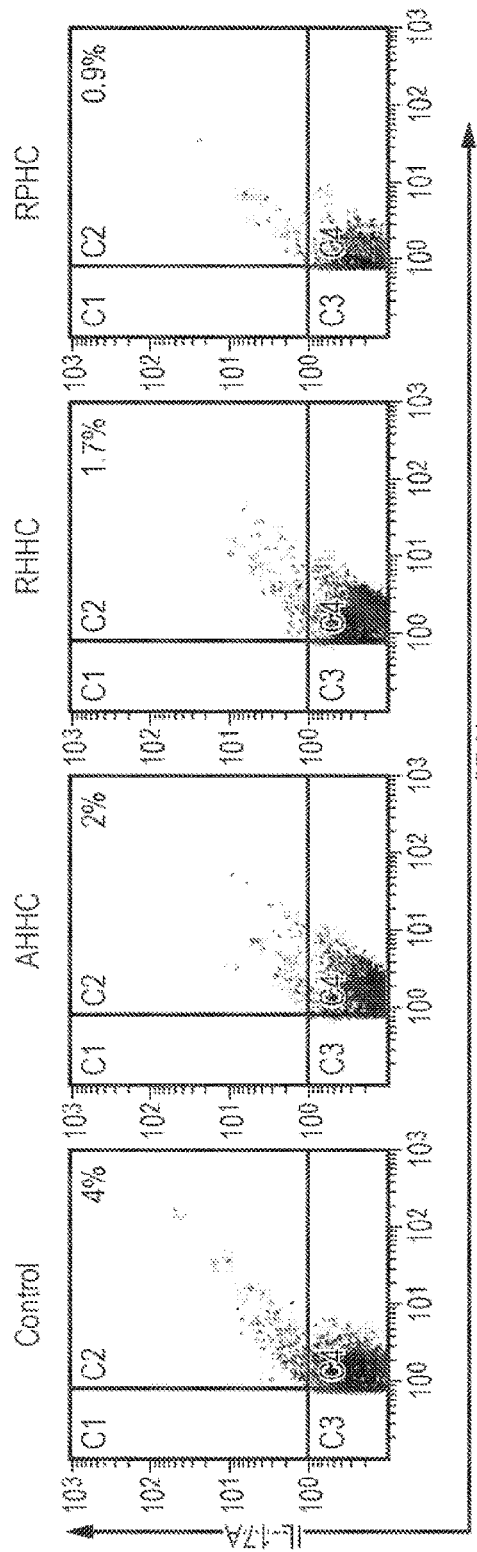
Fig. 6O
Fig. 6P
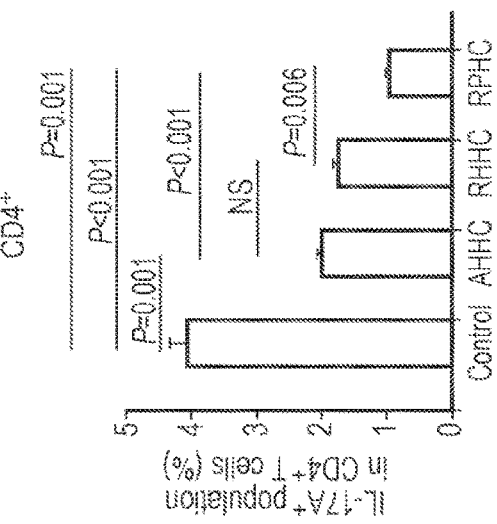
Figs. 6O - 6P

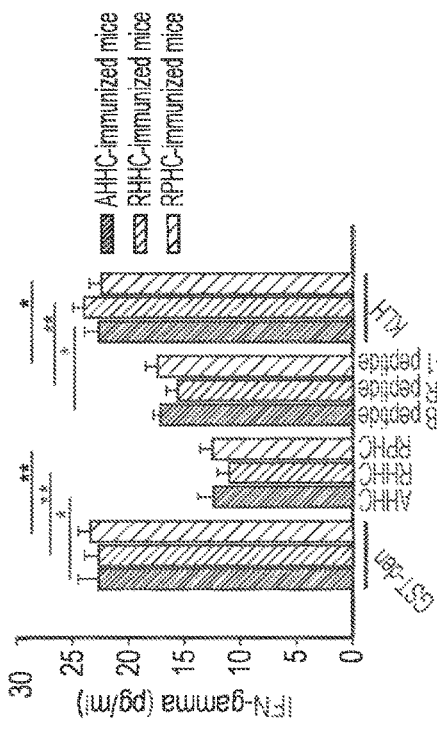
Fig. 7A
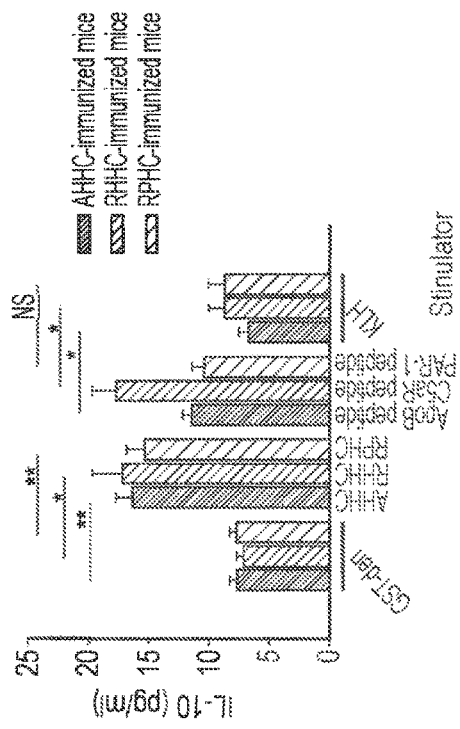
Fig. 7B
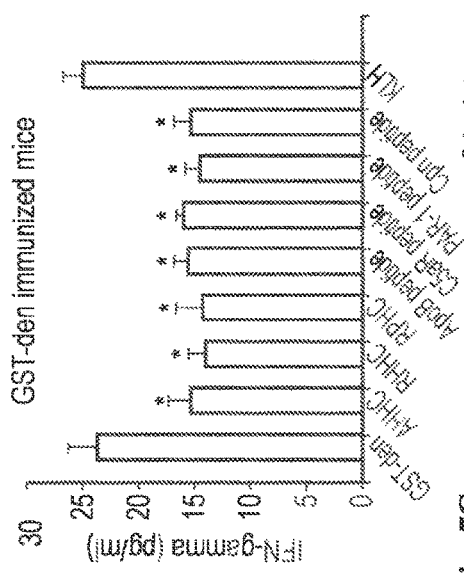
Fig. 7C
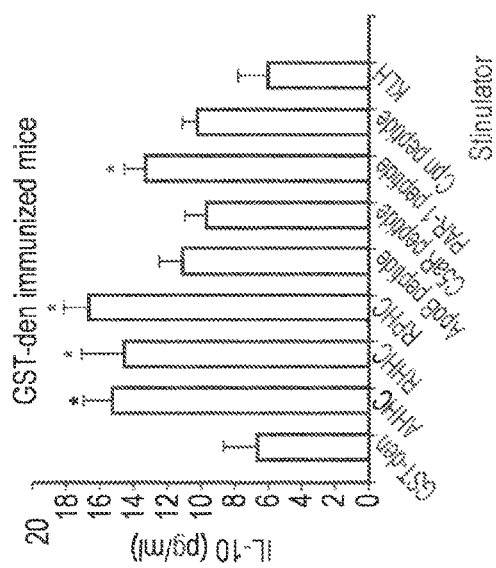
Fig. 7D
Fig. 7A - 7D Fig. 8A
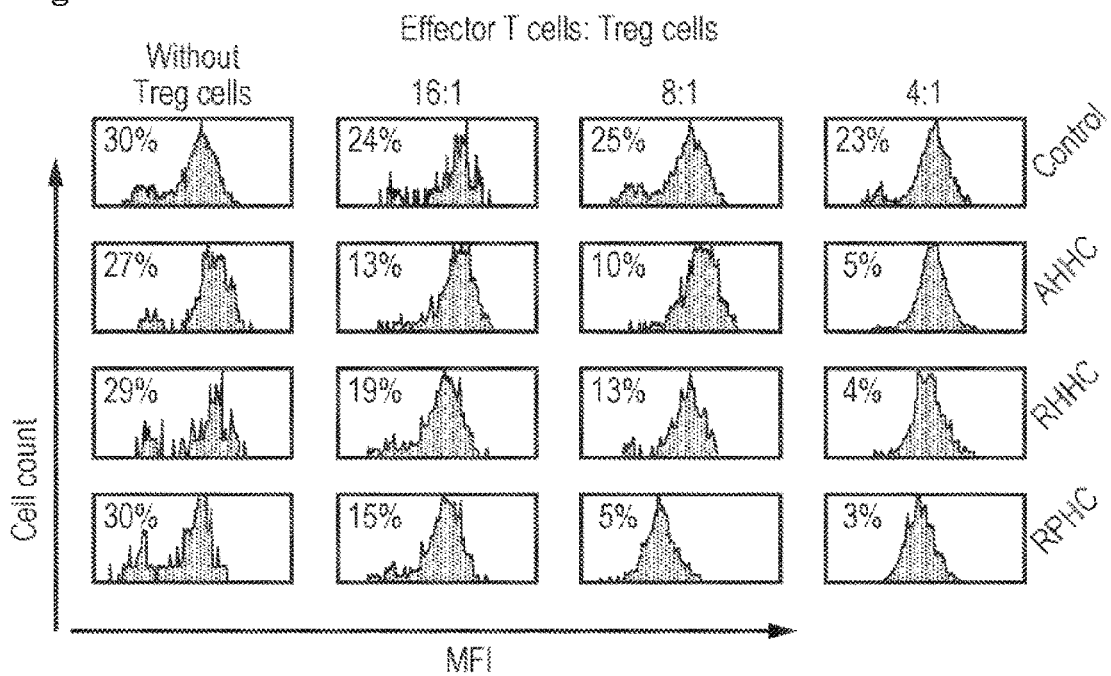
Fig. 8B
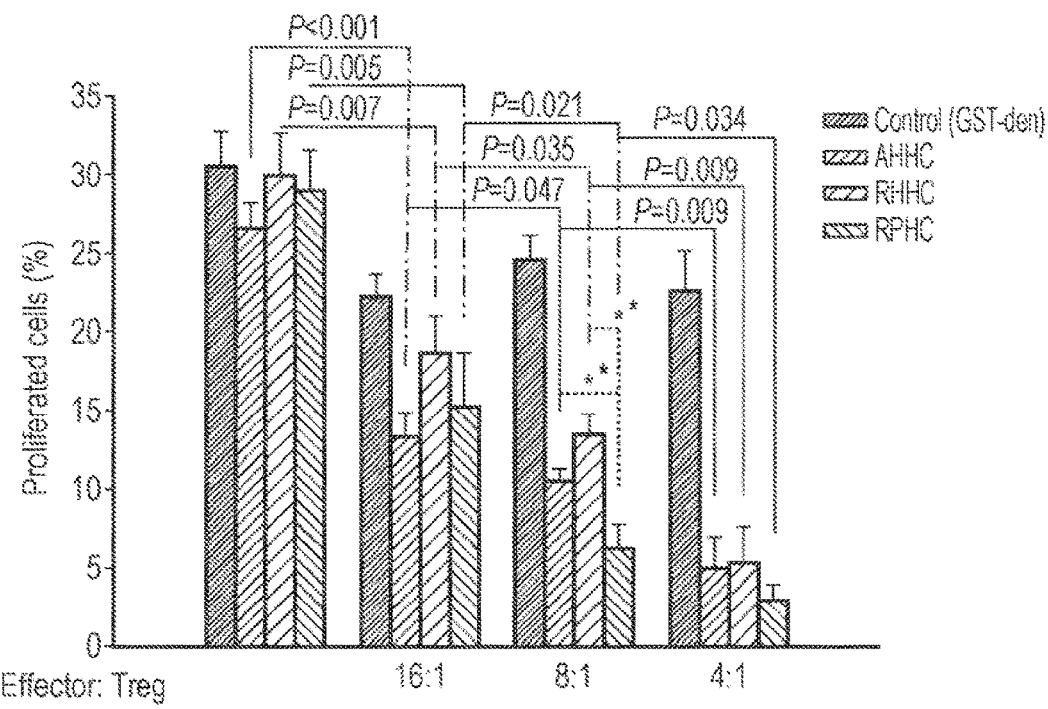
Figs. 8A - 8B

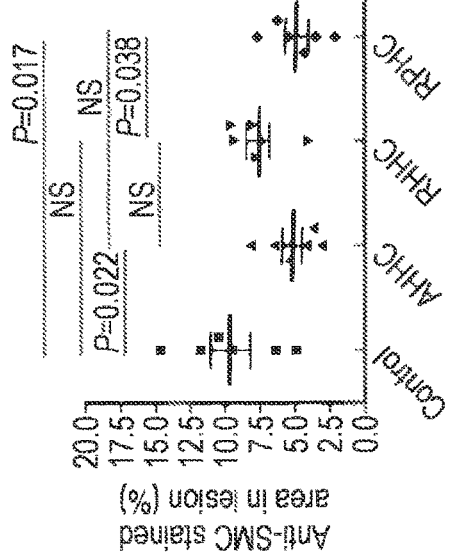
Fig. 9A
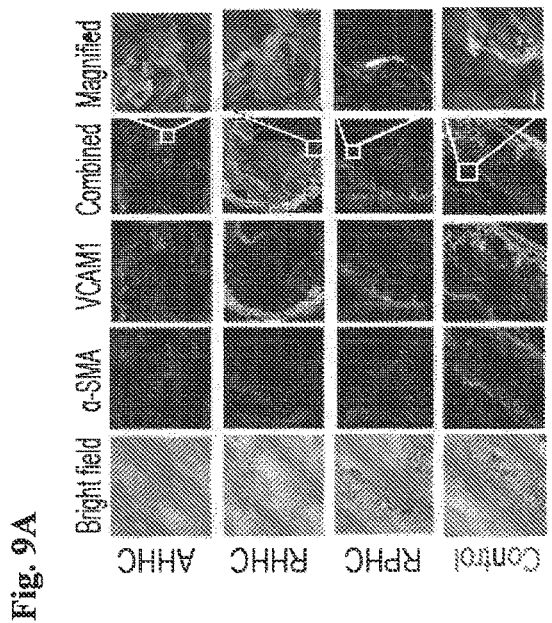
Fig. 9B
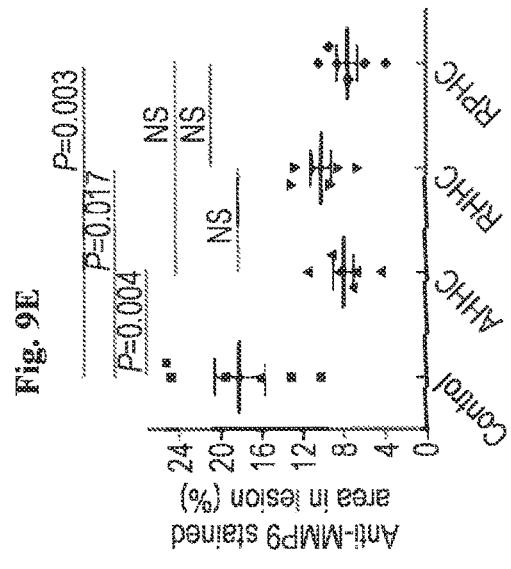
Fig. 9C
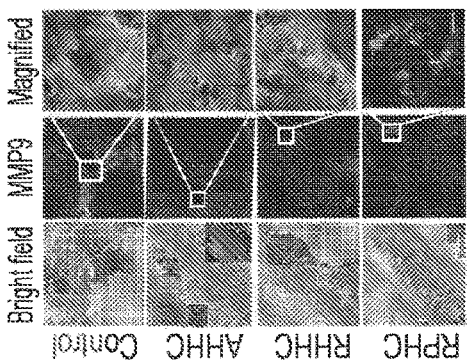
Fig. 9D
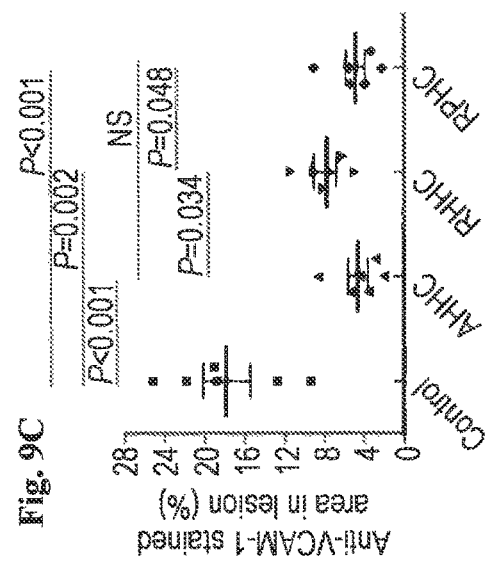
Fig. 9E
Fig. 9A - 9E Fig. 10A
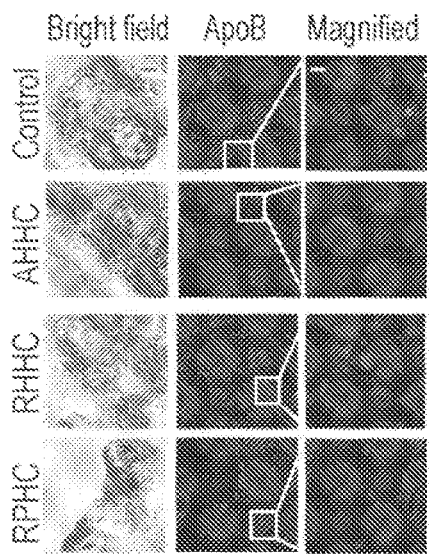
Fig. 10B
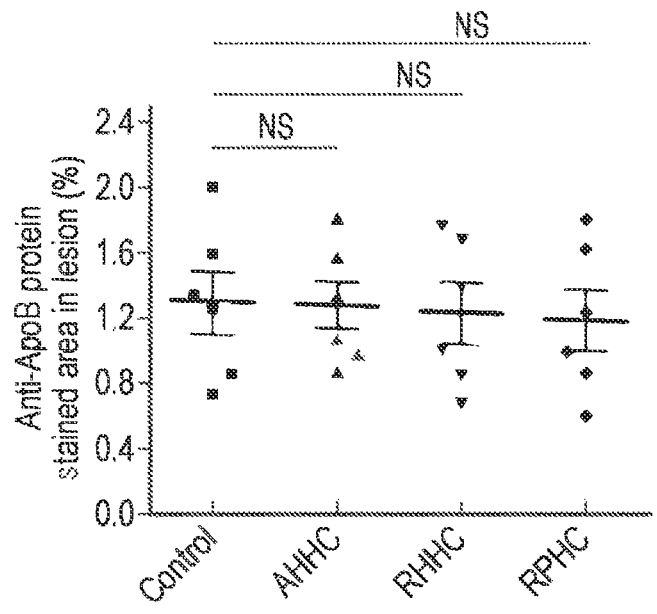
Fig. 10C
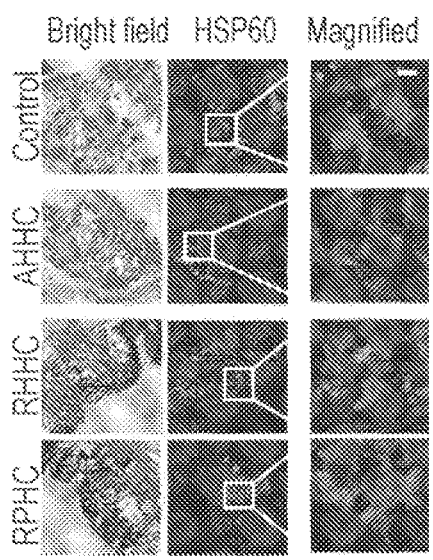
Fig. 10D
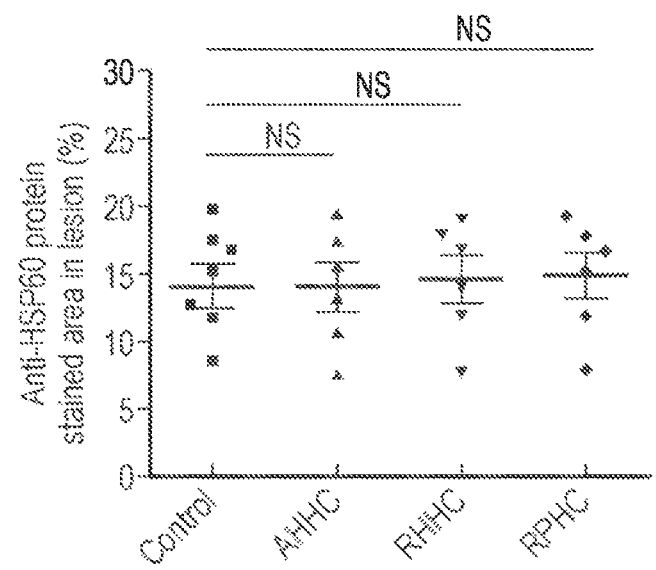
Fig. 10A - 10D Fig. 11A
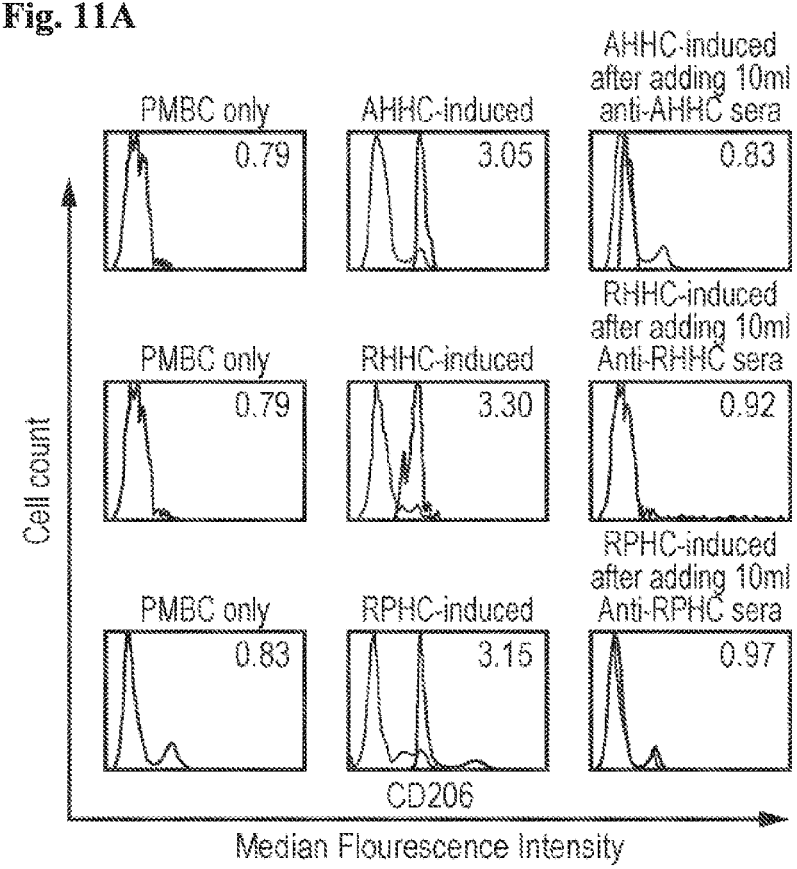
Fig. 11B
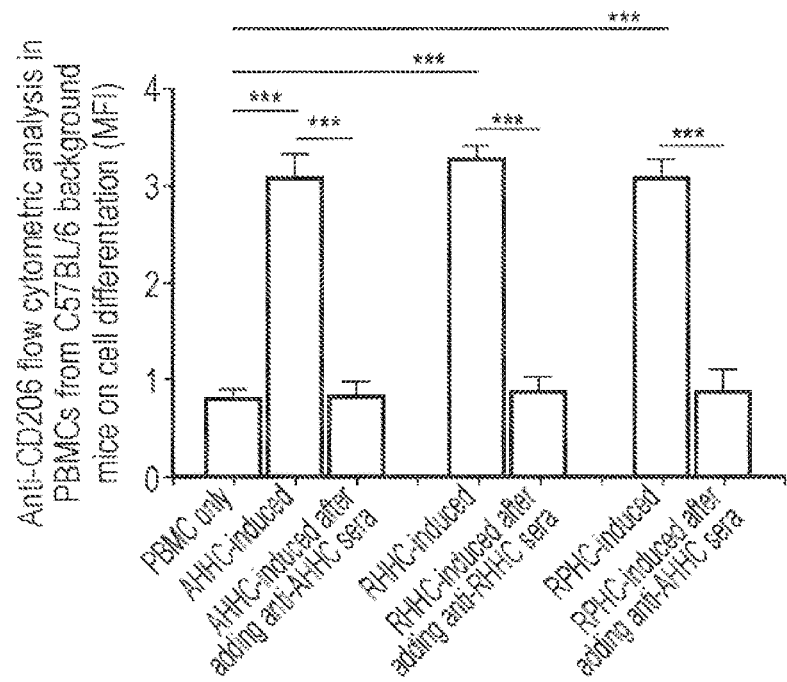
Figs. 11A - 11B Fig. 11C
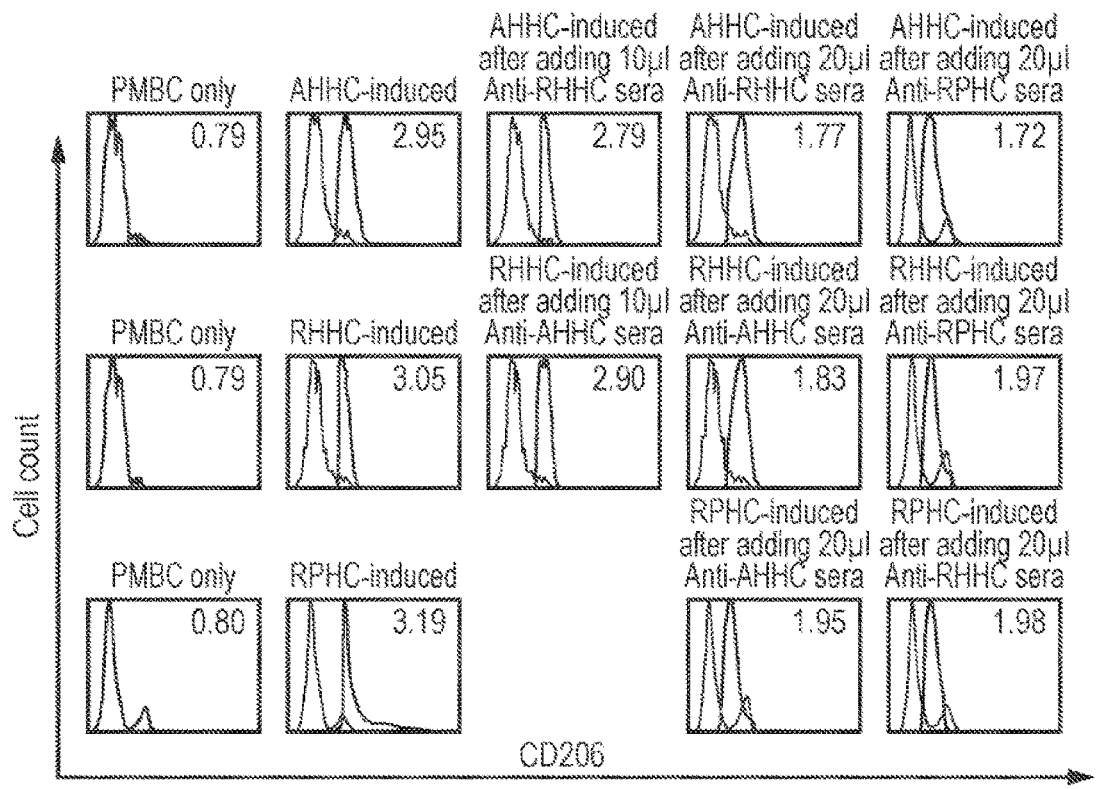
Fig. 11D
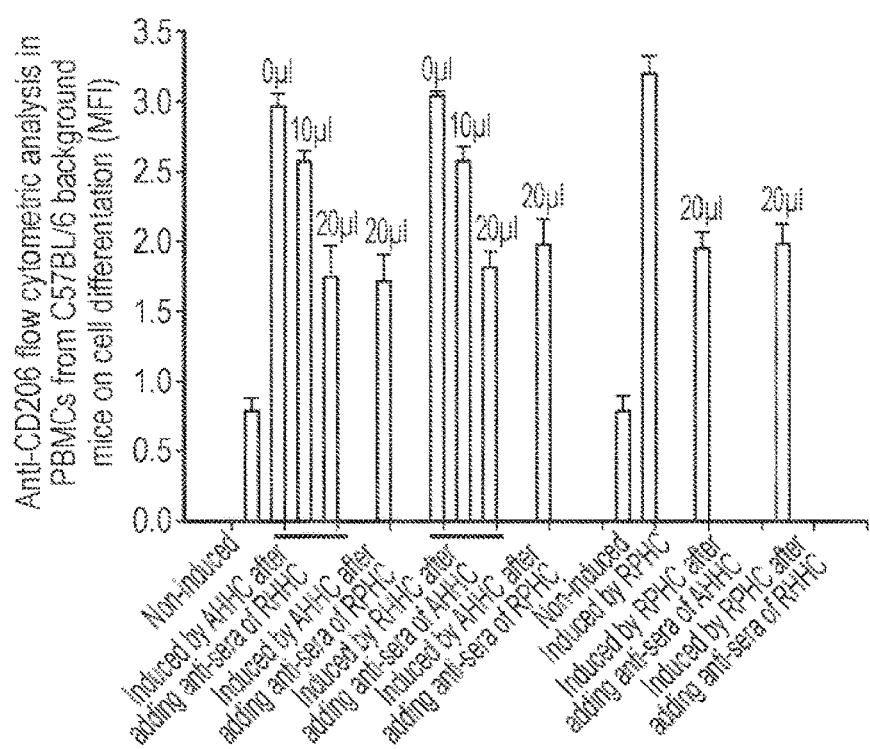
Figs. 11C - 11D

Fig. 12A
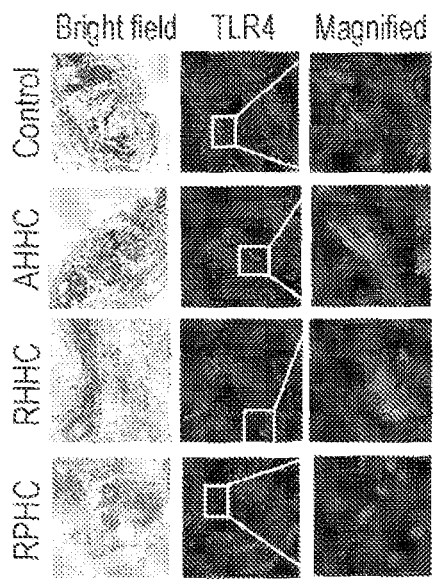
Fig. 12B
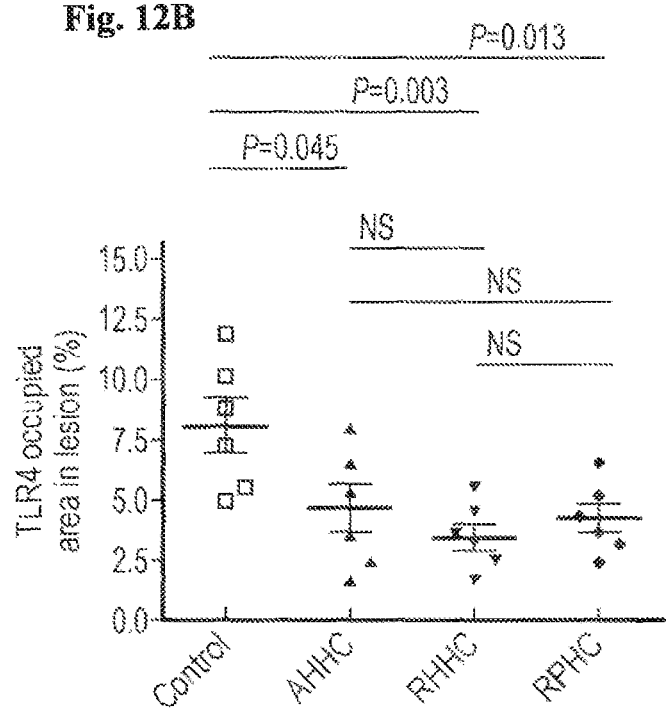
Fig. 12C
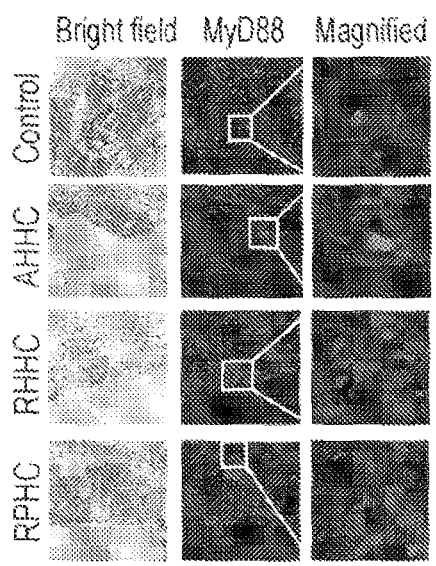
Fig. 12D
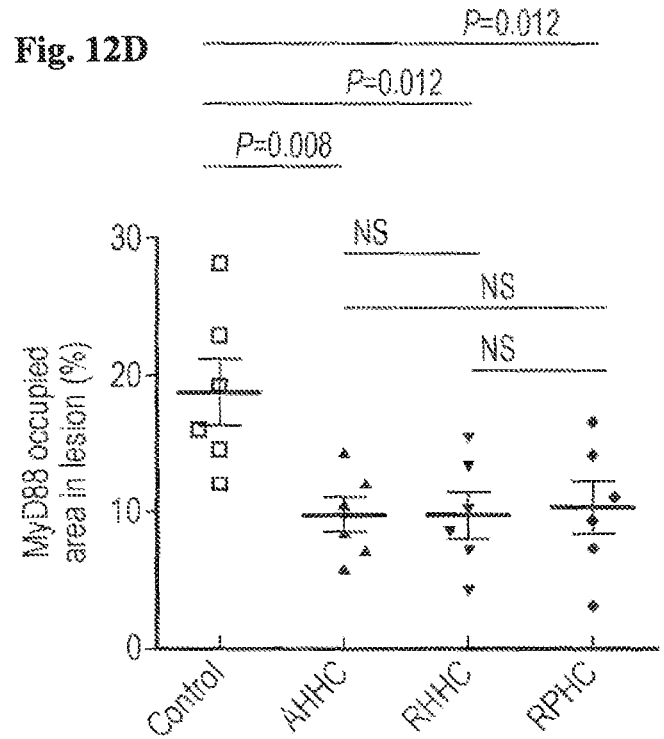
Figs. 12A - 12D Fig. 13A
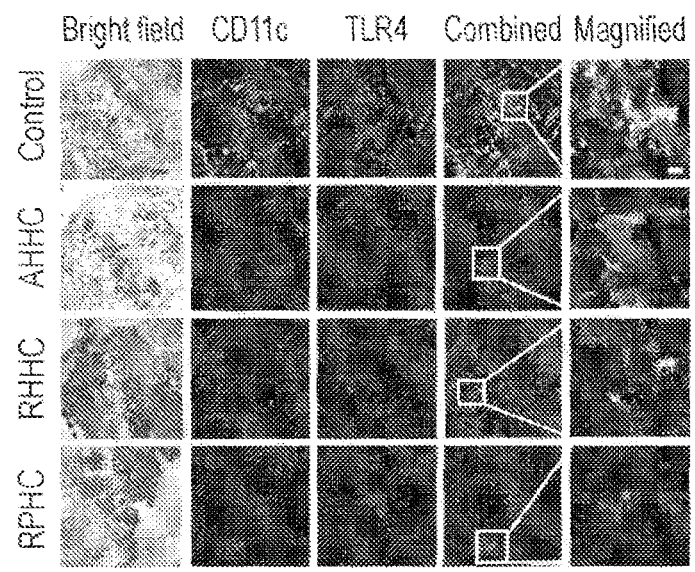
Fig. 13B
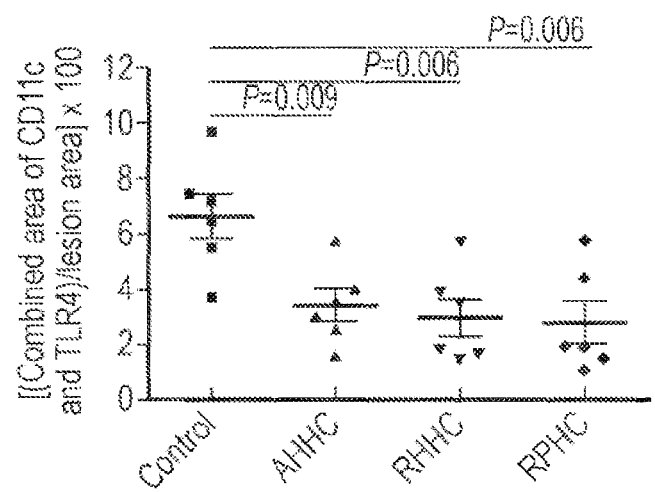
Figs. 13A - 13B Fig. 13C
*Statistical analysis of the effect of immunization with the peptides*

| | AHHC (A) | RHHC (B) | RPHC (C) | Statistical analysis |
|---|---|---|---|---|
| Lesion occupied areas in aortas $(\mu m)^2$ | 31071 | 24123 | 21386 | B vs A, P<0.01; C vs A, P<0.01 |
| Lesion reduction in aortas (%) | 55.9 | 66.4 | 68.9 | B vs A, P<0.01; C vs A, P<0.01 |
| Lesion occupied areas in descending aortas (%) | 8.4 | 6.6 | 6.4 | B vs A, P<0.05; C vs A, P<0.01 |
| Lesion reduction in descending aortas (%) | 57.3 | 66.1 | 67.3 | NS |
| Collagen content in lesions (%) | 18.6 | 19.4 | 24.4 | C vs A, P<0.01; C vs B, P<0.01 |
| Macrophage-occupied area in lesion (%) | 14.9 | 13.6 | 10.3 | C vs A, P<0.05 |
| Dendritic cell-occupied area (%) | 13.3 | 10.5 | 7.9 | C vs A, P<0.05 |
| $CD4^+$ T cell expressing Foxp3 (%) in lesion | 8.2 | 9.4 | 9.9 | NS |
| $CD4^+$ T cell expressing Foxp3 (%) in splenocytes | 13.3 | 15.3 | 18.0 | C vs A, P<0.01 |
| $CD4^+$ expressing IL-10 in lesions | 4.8 | 5.2 | 5.9 | NS |
| TNF-α-occupied areas in lesions | 25.7 | 15.2 | 15.6 | B vs A, P<0.01; C vs A, P<0.05 |
| IL-10 in plasma (pg/ml) | 10.0 | 12.3 | 15.9 | C vs A, P<0.01 |
| TGF-β in plasma (pg/ml) | 23.0 | 24.3 | 27.2 | C vs A, P<0.01; C vs B, P<0.05 |
| TNF-α in plasma (pg/ml) | 209 | 200 | 180 | C vs A, P<0.001; C vs B, P<0.01 |
| IFN-γ in plasma (pg/ml) | 20.8 | 19.3 | 18 | C vs A, P<0.01 |
| IL-10 in supernatants of splenocytes (pg/ml) stimulated with 10 μg/ml ConA | 34 | 38 | 40 | NS |
| TGF-β in supernatants of splenocytes (pg/ml) stimulated with 10 μg/ml ConA | 35 | 39 | 43 | NS |
| TNF-α in supernatants of splenocytes (pg/ml) stimulated with 10 μg/ml ConA | 217 | 209 | 195 | NS |
| IFN-γ in supernatants of splenocytes (pg/ml) stimulated with 10 μg/ml ConA | 45 | 44 | 42 | NS |
| $IL-4^+$ expressing $CD4^+$ T cells (%) | 2.7 | 2.8 | 2.8 | NS |
| $IL-17A^+$ expressing $CD4^+$ T cells (%) | 2 | 1.7 | 0.9 | C vs A, P<0.001; C vs B, P<0.01 |
| $IL-2^+$ expressing $CD4^+$ T cells (%) | 4 | 3 | 3 | C vs A, P<0.01; C vs B, P<0.05 |
| Smooth muscle cell expression in lesion (%) | 5.2 | 7.6 | 4.9 | C vs A, P<0.05 |
| VCAM-1 (%) | 4.5 | 7.8 | 4.8 | B vs A, P<0.05; C vs B, P<0.05 |
| MMP9 (%) | 7.9 | 10.1 | 7.6 | NS |
| TLR4 (%) | 4.6 | 3.4 | 4.2 | NS |
| MyD88 (%) | 9.7 | 9.6 | 10.2 | NS |

NS: denotes not significant

SEQ ID NO:1

Arg Ile Cys Tyr Asn His Leu Gly Thr Lys Pro Pro Thr Thr Glu Thr
1               5                   10                  15
Cys Gln Glu Asp Ser Cys Tyr Lys Asn Ile Trp Thr Phe Asp Asn Ile
            20                  25                  30
Ile Arg Arg Gly Cys Gly Cys Phe Thr Pro Arg Gly Asp Met Pro Gly
        35              40                  45
Pro Tyr Cys Cys Glu Ser Asp Lys Cys Asn Leu
    50                  55

FIG. 14A

SEQ ID NO:2

TLQ    KKIEEIAAKY    KHSVVKKCCY    DGACVNNDET    CEQRAARISL    GPRCIKAFTE
CCVVASQLRA    NISHKDMQLG    R

FIG. 14B

SEQ ID NO:6

1 MNSFNYTTPD YGHYDDKDTL DLNTPVDKTS NTLRVPDILA LVIFAVVFLV GVLGNALVVW
 61 VTAFEAKRTI NAIWFLNLAV ADFLSCLALP FLFTSIVQHH HWPFGGAACS ILPSLLLLNM
121 YASILLLATI SADRFLLVFK PIWCQNFRGA GLAWIACAVA WGLALLLTIP SFLYRVVREE
181 YFPPKVLCGV DYSHDKRRER AVAIVRLVLG FLWPLLTLTI CYTFILLRTW SRRATRSTKT
241 LKVVVAVVAS FFIFWLPYQV TGIMMSFLEP SSPTFLLLNK LDSLCVSFAY INCCINPIIY
301 VVAGQGFQGR LRKSLPSLLR NVLTEESVVR ESKSFTRSTV DTMAQKTQAV

MULTI-EPITOPIC CONSTRUCT

CROSS REFERENCE TO RELATED APPLICATIONS

This application claims priority to International Application No. PCT/GB2016/050150 filed on Jan. 25, 2016 which claims priority to a GB Application No. 1501354.4 filed on Jan. 27, 2015 and GB Application No. 1510195.9 filed on Jun. 11, 2015, which is hereby incorporated by reference in their entireties.

INCORPORATION OF SEQUENCE LISTING

A paper copy of the Sequence Listing and a computer readable form of the Sequence Listing containing the file named "P135165us_Substitute_Sequence_Listing.txt", which is 7,687 bytes in size (as measured in MICROSOFT WINDOWS® EXPLORER), are provided herein and are herein incorporated by reference. This Sequence Listing consists of SEQ ID NOs: 1-19.

This invention relates to multiple epitope constructs, immunogenic and vaccine compositions comprising recombinant molecules presenting inserted multiple and different epitopes from a variety of antigens. In particular, the invention relates to such compositions for eliciting an immune response against antigens and pathogens involved in the development of atherosclerosis the invention includes inter alia methods of treating and/or preventing the disease and recombinant protein products.

BACKGROUND

Atherosclerosis is increasingly recognized as a complex chronic inflammatory disease of the arterial walls as evidenced by the presence of inflammatory cells, activated immune cells and cytokines in lesions, all of which indicate involvement of the immune system. Dendritic cells (DCs) are likely to play a crucial role in directing innate and adaptive immunity. A major component of the innate response involves the entry of monocytes into nascent lesions, followed by differentiation of monocytes into macrophages and CD11c$^+$ cells with DC-like properties. Atherosclerotic plaques are known to contain macrophage-derived foam cells in which macrophages interact with T cells to produce a wide array of cytokines that can exert both pro- and anti-inflammatory effects. Although the molecular mechanism responsible for the development of atherosclerosis is not completely understood, it is clear that the immune system plays a key role in the development of the atherosclerotic plaque and in its complications. Consequently, several antigenic stimuli that are associated with the pathogenesis of atherosclerosis based on modified self-molecules or peptides derived from these molecules such as oxidized low-density lipoproteins (oxLDLs) [9,10], β2-glycoprotein I (β2GP1), phosphatidylcholine (PC) [11,12], heat shock proteins (HSPs), have been reported. Many more studies related to vaccination against atherosclerosis apart from using epitopes from these self-antigens have also demonstrated high efficacy against atherosclerotic lesion formation for other antigens. However, one of the difficulties in developing effective vaccination strategies against atherosclerosis is the selection of a specific antigen.

In the discovery and development of potential antigens, it has been demonstrated that immunization of B6;129S-Ldelr$^{tm1Her}$Apob$^{tm2Sgy}$/J mice with the recombinant construct termed "AHHC" containing epitopes derived from apolipoprotein B (ApoB), heat shock protein (HSP) 60 and proteins of *Chlamydia pneumoniae* (Cpn), reduced atherosclerotic lesion formation in the mice fed with high-fat diet (HFD) (Lu et al 2012; Atherosclerosis 225: 56-68). In addition, it is known from the prior art that immunization with peptides derived from the N-terminal of complement component 5a receptor (C5aR) reduced early atherosclerotic lesion development in B6;129S-Ldelr$^{tm1Her}$Apob$^{tm2Sgy}$/J mice (Lu et al 2012; Arterioscler Thromb Vasc Biol 32: 2358-2371). Furthermore, in preclinical studies, protease-activated receptor (PAR)-1 inhibition showed a strong anti-thrombotic effect, leading to a significant decrease in platelet aggregation, whereas primary haemostatic function was preserved (Chintala et al 2010 Arterioscler Thromb Vasc Biol 30: 2143-2149).

The human complement system is a key component of the innate host defense directed against invading pathogens. C5a is a protein fragment released from complement component C5 and is a 74 amino acid peptide in humans that is generated by the cleavage of C5a convertase on the C5 α-chain during the classical, alternative, and lectin pathways of complement activation. C5a mediates its effects via its G protein-coupled C5a receptor (C5aR/CD88) on the plasma membrane of target cells triggering intracellular signaling, which results in chemotaxis, a respiratory burst and release of pro-inflammatory mediators from granulocytes. C5a attracts and activates neutrophils, monocytes, and platelets and stimulates the release of inflammatory mediators, including reactive oxidants, proteolytic enzymes, chemokines, cytokines, and complement factors C3 and properdin. Secretion of C3 and properdin by neutrophils, as well as the presence of apoptotic and necrotic decidual tissue, and may accelerate alternative pathway activation creating a proinflammatory amplification loop at sites of leukocyte infiltration that enhances C3 activation and deposition and generates additional C5a. Human C5aR is an integral membrane glycoprotein, consisting of 350 amino acids forming a single poly-peptide chain. C5a/C5aR interactions have been shown to modify the production of IL-12, thus regulating Th-1 cell responses, and to potentiate the production of cytokines such as IL-6, IL-8, and TNF-alpha. The C5aR is expressed abundantly on leukocytes, including neutrophils, monocytes, eosinophils, and lymphocytes. C5aR is also expressed by a wide range of parenchymal cells, including glomerular mesangial and proximal tubular epithelial cells. Parenchymal C5aR expression has been shown to be enhanced in areas of acute inflammation.

Ruptured or vulnerable plaques of atherosclerosis are usually characterized by the presence of a large lipid core, a reduced number of smooth muscle cells, a thin fibrous cap, and an increased number of inflammatory cells, such as macrophages and T cells. Macrophages are thought to play a major role in plaque destabilization and rupture. Through the production of matrix metalloproteinases (MMPs), these cells are capable of degrading components of the extracellular matrix, such as collagen, proteoglycans, and elastin. Several studies have shown by immunohistochemistry and in situ zymography that MMP-1, MMP-3, and MMP-9 are present in the shoulder region of atherosclerotic plaques, and it has been shown that overexpression of active MMP-9 in apoE-deficient mice induces plaque disruption. The stimulatory effect of C5a on the expression of MMP-1 and MMP-9 mRNA in monocyte-derived macrophages isolated from different donors and in human macrophages isolated from atherosclerotic plaques has also been reported.

There is accumulating clinical and experimental data point to an involvement of the anaphylatoxin C5a in the pathogenesis of atherosclerosis. It has recently been reported that there is a predictive value of C5a plasma levels for cardiovascular events in patients with advanced atherosclerosis. Receptors for C5a were detected in atherosclerotic lesions. Furthermore, C5a induces the expression of adhesion molecules by endothelial cells. C5a activates macrophages, causing them to release the inflammatory mediators TNF-alpha, interleukin-1. TNF-alpha, on the other hand, directly induces MMP expression in these cells.

In the discovery and development of potential antigens, it has been demonstrated that immunization of B6;129S-Ldelr$^{tm1Her}$Apob$^{tm2Sgy}$/J mice with the recombinant construct termed "AHHC" containing epitopes derived from apoipoprotein B ApoB), heat shock protein (HSP) 60 and proteins of Chlamydia pneumoniae (Cpn), reduced atherosclerotic lesion formation in the mice fed with high-fat diet (HFD) (Lu et al 2012; Atherosclerosis 225: 56-68). In addition, it is known from the prior art that immunization with peptides derived from the N-terminal of complement component 5a receptor (C5aR) reduced early atherosclerotic lesion development in B6;129S-Ldelr$^{tm1Her}$Apob$^{tm2Sgy}$/J mice (Lu et al 2012; Arterioscler Thromb Vasc Biol 32: 2358-2371). Furthermore, in preclinical studies, protease-activated receptor (PAR)-1 inhibition showed a strong anti-thrombotic effect, leading to a significant decrease in platelet aggregation, whereas primary haemostatic function was preserved (Chintala et al 2010 Arterioscler Thromb Vasc Biol 30: 2143-2149).

There is a need for improved treatments for arteriosclerotic vascular disease.

BRIEF SUMMARY OF THE DISCLOSURE

According to a first aspect of the invention there is provided a recombinant construct comprising:
i) a scaffold portion and incorporated therein;
ii) a first species of epitope capable of eliciting an anti-arteriosclerotic vascular disease response via a first pathway; and
iii) a second species of epitope capable of eliciting an anti-arteriosclerotic vascular disease response via a second pathway that is independent from said first pathway.

Reference herein to the first and second pathways being "independent" form one another is intended to infer that the formation of atherosclerosis via either the first or second pathway is by different mechanisms of action or causal routes.

Preferably, the scaffold portion is native dendroaspin and comprises an amino acid sequence selected from SEQ ID NO:1 (FIG. 14A).

Preferably, first pathway to atherosclerosis formation is via a C5 interaction and more preferably by a C5a or C5aR pathway. The C5 epitope is therefore a C5a epitope or a C5a receptor (C5aR) epitope. The C5 epitope may comprise from 5 to 40, e.g. from 8 to 40 amino acid residues or for example from 8 to 35 amino acid residues. The C5a epitope may comprise from 5 to 40 contiguous amino acid residues selected from the C5a sequence (SEQ ID NO:2) (FIG. 14B), e.g. from 8 to 40 amino acid residues, for example from 8 to 35 amino acid residues. In one embodiment, the C5a epitope comprises from 8 to 20, e.g. 8 to 15 contiguous amino acid residues selected from the C5a sequence.

Preferably, the C5a epitope is a polypeptide comprising, or consisting of, the amino acid sequence selected from the group comprising EQRAARISLGPR (SEQ ID NO:3), RAARISLGPRCIKAFTE (SEQ ID NO:4) and CVNNDE-TCEQ (SEQ ID NO:5) or a functional fragment thereof that has antigenic activity. For example, the epitope may comprise a sequence of from 5 to 40 contiguous amino acid residues selected from the C5a sequence and comprising SEQ ID NOs: 2, 3 or 4.

Preferably, the C5aR epitope comprises from 5 to 50 contiguous amino acid residues selected from the C5aR sequence (SEQ ID NO:6; FIG. 14C), for example from 10 to 40 amino acid residues or for example from 14 to 35 amino acid residues. In one embodiment, the C5aR epitope comprises from 1 to 31 contiguous amino acid residues or a functional fragment thereof.

Preferably, the C5aR epitope may be at the N-terminal end (containing free amino group) or the C-terminal end (containing free carboxyl group) of the C5aR amino acid sequence. Alternatively and more preferably the C5aR epitope is a polypeptide comprising, or consisting of, an amino acid sequence selected from the group comprising MNSFNYTTPDYGHYDDKDTLD (SEQ ID NO:7), TLD-LNTPVDKTSN (SEQ ID NO:8) and MNSFNYTTPDYGHYDDKDTLDLNTPVDKTSN (SEQ ID NO:9) or a functional fragment thereof that has antigenic activity.

Reference herein to a functional fragment encompasses portions of the epitope amino acid sequences that retains sufficient amino acids to provide and act as an antigenic determinant and to possess antigenic activity and thus function as an epitope. A functional fragment also encompasses portions of epitope amino acid sequences that when incorporated and presented in the scaffold portion, elicits an immune response against atherosclerosis that can be determined by, for example and without limitation a reduction in the area occupied by an atherosclerotic lesion.

Reference to a first and second species of epitope is intended to convey that they are each separately and independently associated with different pathways that ultimately lead to atherosclerosis and associated diseases.

Preferably, the recombinant construct comprises more than one first species of epitopes.

Preferably, the second species of epitope is a human epitope. The second species of epitope may comprise from 5 to 40, e.g. from 9 to 40 amino acid residues, for example from 9 to 20 amino acid residues. Preferably, the second species of epitope associated with an anti-arteriosclerotic vascular disease response is selected from the group comprising, or consisting of apolipoprotein (Apo) epitopes, heat-shock protein (HSP) epitopes, chlamydia pneumonia epitopes, protease-activated receptor-1 epitopes (PAR-1) and perilipin epitopes.

More preferably, the second epitope is a heat-shock protein (HSP) epitope, chlamydia pneumonia epitope, tissue factor or PAR-1 epitope.

Preferably, said heat-shock protein (HSP) is a HSP 60 or a HSP 65. More preferably said HSP 60 is a human HSP 60 or a Mycobacterium bovis HSP. More preferably said epitope capable of eliciting a response against HSP 60 is a polypeptide comprising, or consisting of the amino acid sequence selected from the group comprising peptide 1 (AA) 153-160: AELKKQSK; (SEQ ID NO:10), peptide 1 (AA) 153-163: AELKKQSKPVT; (SEQ ID NO:11), peptide 1 (AA) 303-312: PGFGDNRKNQ (SEQ ID NO:12), peptide 2: AA 277-286 PGFGDNRKNQ (SEQ ID NO:13), peptide (AA) 516-528) KGIIDPTKWRTA (SEQ ID NO:14), and mycobacterium (AA) 253-268: EGEALSTLVVNKIRGT (SEQ ID NO 15) or a functional fragment thereof that has antigenic activity.

Preferably, said chlamydia pneumonia is Cpn1 or Cpn2. More preferably, said epitope capable of eliciting a response against Cpn is a polypeptide comprising, or consisting of the amino acid sequence selected from the group comprising the major outer membrane protein (MOMP) (amino acid sequence (AA) 67-74: GDYVFDRI (SEQ ID NO:16), and putative outer membrane protein (Pomp) 5 of Cpn (amino acid sequence (AA) 283-291: QAVANGGAI (SEQ ID NO:17) or a functional fragment thereof that has antigenic activity.

Preferably, the tissue factor epitope is (AA56-67) and comprises the sequence EWEPKPVNQVYT (SEQ ID NO:19).

Preferably, the PAR-1 epitope is (AA42-55) and comprises the amino acid sequence SFLLRNPNDKYEPF (SEQ ID NO:19).

Preferably, the recombinant construct of the present invention comprises more than one second epitope for example it may comprises 2, 3, 4, 5, 6, 7, 8, 9 or 10 identical or different second epitopes. For example in particularly preferred embodiments the recombinant construct may comprise a C5aR epitope, a Cpn epitope and two different HSP epitopes or it may comprise a C5aR epitope, a Cpn epitope, a HSP epitope and a PAR-1 epitope.

Preferably, the amino acid sequences of the first and/or second epitope are incorporated into (a) loop I and/or loop II; (b) loop I and/or loop III; (c) loop II and/or loop III; or (d) loop I, loop II and loop III of the dendroaspin scaffold. Loop I comprises amino acid residues 4-16, loop II residues 23-36 and loop III residues 40-50. However, the further amino acids being incorporated may extend into or substitute regions external to the loops, i.e. residues 1-3, 17-22 and 37-39 such that residues of the non-loop regions are augmented or substituted for those of the further amino acid sequence or sequences being inserted. The further amino acid residues are preferably incorporated into either loop I or loop II. In this way the RGD-containing loop III is unaltered and so the integrin binding function of dendroaspin is retained. A preferred location for the inserted further sequence is at a site in dendroaspin scaffold between amino acid residues: 4-16, 18-21, 23-36, or 52-59. Each inserted further amino acid sequence or portion of a further amino acid sequence is preferably an amino acid sequence in the range 3-40 amino acid residues, more preferably 3-16, even more preferably 3-14 amino acid residues long. The start of the inserted further amino acid sequence may be at any one of amino acid residues 1-57 of the dendroaspin scaffold. The end of the inserted further amino acid sequence may be at any one of amino acid residues 3-59 of the dendroaspin scaffold.

When two or more further amino acid sequences are inserted into the dendroaspin scaffold then the linear distance between these is preferably in the range 1-35 amino acids, more preferably 1-14 amino acids. When more than two or more further amino acid sequences are inserted then there is preferably at least one native dendroaspin amino acid residue separating each further amino acid sequence. The RGD-containing loop may be modified by insertion, deletion or substitution of one of more amino acid residues, preferably a maximum of 8 or a minimum of 1 amino acids can be modified within loop III of dendroaspin. Loop I and/or loop II may be modified by insertion, deletion or substitution of one or more amino acid residues. Any suitable number of amino acids can be inserted into the dendroaspin scaffold to give the desired bi- or multi-functional activity although a number of residues in the range 14 to 36 are preferred for insertion at one or more sites in the dendroaspin scaffold.

Preferably, in some embodiments of the invention the first or second epitopes may be attached at either or both of the C and/or N terminus ends of the dendroaspin scaffold protein.

In a further aspect of the invention there is provided an expression vector comprising the nucleic acids encoding the proteins incorporated into the construct of the first aspect of the invention.

In a yet further aspect of the invention there is provided an antigenic composition comprising the protein according to the first aspect of the invention and an antigenic hydrophobic complex.

In a yet further aspect of the invention there is provided a pharmaceutical composition comprising the immunogenic composition of the present invention, formulated as an injectable or oral product. Preferably, the pharmaceutical composition further includes a suitable adjuvant, excipient, diluent and/or carrier.

In a yet further aspect of the invention there is provided a pharmaceutical composition comprising the protein of the first aspect of the invention, the vector of the invention or the immunogenic composition of the invention.

In a yet further aspect of the invention there is provided the protein of the first aspect of the invention or the vector of the invention for use as a medicament.

In a yet further aspect of the invention there is provided a method of eliciting an anti-atherosclerosis response in a mammal comprising administering a product selected from: the recombinant protein according to the first aspect of the invention; the vector of the invention; the immunogenic composition of the invention; the pharmaceutical composition of the invention; and the pharmaceutical composition of the invention.

In a yet further aspect of the invention there is provided a method of treating, preventing or reducing atherosclerosis comprising administering to an individual a product selected from: the recombinant protein according to the first aspect of the invention; the vector of the invention; the immunogenic composition of the invention; the pharmaceutical composition of the invention; and the pharmaceutical composition of the invention. The product may be administered in a therapeutically effective amount or therapeutically acceptable amount.

In a yet further aspect of the invention there is provided a method of treating an individual with early stage atherosclerosis or an individual identified as at risk of developing atherosclerosis, the method comprising administering to an individual a product selected from: the recombinant protein according to the first aspect of the invention; the vector of the invention; the immunogenic composition of the invention; the pharmaceutical composition of the invention; and the pharmaceutical composition of the invention. The product may be administered in a therapeutically effective amount or therapeutically acceptable amount.

In a yet further aspect of the invention there is provided a vaccine comprising the protein according to the first aspect of the invention or the vector of the invention.

In a yet further aspect of the invention there is provided a method of eliciting an immune response against epitopes associated with at least two independent pathways associated with atherosclerosis formation, the method comprising:
  (i) constructing and expressing a dendroaspin scaffold protein comprising at least one first and at least one second epitope as herein before described;
  (ii) incubating eukaryotic cells with said dendroaspin scaffold protein;
  (iii) using said eukaryotic cells to prepare microsomes;

(iv) incorporating said microsomes and dendroaspin scaffold protein with one or more pharmaceutically acceptable constituents to produce an orally or injectable administratable preparation; and (v) administering said preparation to a mammal or human.

Data has shown that immunization with ApoB/PAR-1/HSP/Cpn did not affect C5a expression in sclerotic lesion, suggesting that C5/C5aR presents an independent pathway in lesion formation. The present invention provides methods and products for advantageously targeting, simultaneously, both the independent C5 and ApoB/PAR-1/HSP/Cpn related pathways in order to provide improved treatments for the prevention and reduction of early stage atherosclerosis.

It will be appreciated that the preferred features ascribed to the first aspect of the invention are applicable mutatis mutandis to each and every other aspect of the invention.

BRIEF DESCRIPTION OF THE DRAWINGS

Embodiments of the invention are further described hereinafter with reference to the accompanying drawings, in which:

FIGS. 1A & 1B show a schematic representation of the backbone of the dendroaspin structure (FIG. 1A) and a schematic representation of alignment of constructs and dendroaspin scaffold (FIG. 1B).

FIGS. 2A-2G show levels of constructed protein-induced IgG, IgG1, and IgG2c antibodies in the sera of B6;129S-Ldlr$^{tm1Her}$Apob$^{tm2Sgy}$/J mice at 2 weeks and 12 weeks respectively, after the first immunization and in controls (GST-Den (referred as GST-den)-immunized mice). The mean optical densities (ODs) and SEM obtained from plasma samples of constructs AHHC, RHHC, and RPHC-immunized mice on Cpn peptide (C)-, hHSP60$^{153-163}$(H), hHSP60$^{303-312}$-(H), C5aR-peptide (R)-, ApoB peptide (A)-, PAR-1(P)-coated ELISA plates are shown. (FIG. 2A) IgG at the dilution ratio: 1:100. (FIG. 2B) IgG1 at the dilution ratio: 1:6250. (FIG. 2C) IgG2c at the dilution ratio: 1:50. (FIG. 2D) Cross reaction between human ApoB peptide-induced antiserum and Cpn peptide. (FIG. 2E) Cross reaction between human ApoB peptide- and hHSP60$^{303-312}$ peptide-induced antiserum and their antigens. (FIG. 2F) Cross reaction between ApoB peptide-induced antiserum and antigens of either PAR-1 peptide or C5aR peptide. (FIG. 2G) Cross reaction between C5aR peptide-induced antiserum and antigens of either ApoB peptide or PAR-1 peptide. Antiserum used for cross-reaction was taken at week 8.

FIGS. 3A-3H show detection and quantitation of the lesion areas in the aorta of B6;129S-Ldlr$^{tm1Her}$Apob$^{tm2Sgy}$/J mice fed on a high-fat diet after immunization with constructs versus controls (GST-den).

FIG. 3A: Photomicrograph of lesions observed in atherosclerotic aortas as analyzed with elastin/van Gieson staining.

FIG. 3B: Scatter plot showing mean of lesion area in the aortic sinus of mice immunized with constructs compared with those in controls (GST-Den). (N=6-9 mice). Error bars=SEM FIG. 3C: Percentage of reduction in lesion size in the aortic sinus (the reduction of control [GST-den] group was set at zero).

FIG. 3D: Representative photomicrographs and quantitative analysis of collagen (Sirius Red coloration under polarized light) in atherosclerotic aortas in individual mice.

FIG. 3E: Quantification of collagen content at lesion area in the aorta of B6;129S-Ldlr$^{tm1Her}$Apob$^{tm2Sgy}$/J mice (N=7 mice). NS: not significant.

FIG. 3F: Representative Oil Red 0-stained en face descending aorta from mice.

FIG. 3G: Percentage of lesion-occupied area versus total area of descending aortas in individual mice (N=6 mice) of the different experimental groups. The mean lesion size and the difference in lesion size between the experimental groups are shown.

FIG. 3H: Percentage of reduction in lesion size in descending aortas (the reduction of control [GST-den] group was set at zero).

FIGS. 4A & 4B show detection and quantitation of the lesion areas in the aorta of B6;129S-Ldlr$^{tm1Her}$Apob$^{tm2Sgy}$/J mice fed on a high-fat diet at week 9 after immunization with constructs versus controls (GST-den), GST and alum. FIG. 4A is a photomicrograph of lesions observed in atherosclerotic aortas as analyzed with elastin/van Gieson staining (N=6-8 mice). FIG. 4B is a scatter plot showing mean of lesion area in the aortic sinus of mice (N=6-8 mice).

FIGS. 5A-5H show the assessment of inflammation-associated cells in the lesions of B6;129S-Ldlr$^{tm1Her}$Apob$^{tm2Sgy}$/J mice fed a high-fat diet after immunization with constructs AHHC, RHHC, and RPHC.

FIG. 5A: Photomicrographs showing IHC staining of CD68 (green) and CD11c (red) markers (scale bar: 100 μm and 12.5 μm for magnified ones).

FIG. 5B: Scatter plot showing anti-CD68-stained area in lesion versus total lesion area; Data are given as the mean of 6 mice.

FIG. 5C: Scatter plot showing anti-CD11c-stained area in lesion versus total lesion area; Data are given as the mean of 6 mice.

FIG. 5D: Co-localization of CD68$^+$ and CD11c$^+$ areas (derived from FIGS. 3B and 3C).

FIG. 5E: Photomicrographs showing IHC staining of CD4$^+$ T-cells (green) and Foxp3$^+$ Treg cells (red) (scale bar: 100 μm and 12.5 μm for magnified ones).

FIG. 5F: Scatter plot showing anti-Foxp3-stained area versus anti-CD4$^+$ stained area in lesion (N=6).

FIG. 5G: Representative analysis of Foxp3 expression by CD4$^+$ T cells in lymph nodes from construct-immunized mice fed on a high-fat diet as assessed using flow cytometry.

FIG. 5H: Percentage of Foxp3$^+$ cells among CD4$^+$ spleen cells as analyzed by flow cytometry. Data are expressed as mean of 3 analyses±SEM. Differences between groups are shown.

FIGS. 6A-6R show the a assessment of IL-10-producing T cells, TNF-α expression in the lesions and cytokine levels in B6;129S-Ldlr$^{tm1Her}$Apob$^{tm2Sgy}$/J mice fed a high-fat diet after immunization with constructs AHHC, RHHC, and RPHC.

FIG. 6A: Photomicrographs showing dual-IHC staining for IL-10 (red) and CD4 (green) (scale bar: 100 μm and 12.5 μm for magnified ones).

FIG. 6B: Scatter plot showing mean of IL-10-positive area co-localized with CD4$^+$ area (%) (N=6).

FIG. 6C: Photomicrographs showing IHC staining for TNF-α (green) of lesions (scale bar: 100 μm and 2.5 μm for magnified ones).

FIG. 6D: Scatter plot showing mean of anti-TNF-α stained area in the lesion versus total lesion area (N=6).

FIG. 6E-H: Cytokine levels measured in plasma.

FIG. 6M; Representative analysis of CD4+IL-4$^+$ T-cells in splenocytes from construct-immunized mice fed on a high-fat diet as assessed by flow cytometer.

FIG. 6N: Percentages of IL-4$^+$ expressing CD4$^+$ spleen cells. Data are expressed as mean of 3 analyses±SEM. Differences between groups are shown.

FIG. 6O: Representative analysis of IL-17A expression by CD4$^+$ T-cells in splenocytes from construct-immunized mice fed on a high-fat diet as assessed by flow cytometry.

FIG. 6P: Levels of IL-17A expression in spleen cells. Data are expressed as mean of 3 analyses±SEM. Differences between groups are shown.

FIG. 6R: Levels of IL-2$^+$ expressing CD4$^+$ in spleen cells. Data are expressed as mean of 3 analyses±SEM. Differences between groups are shown.

FIGS. 7A-D show the measurement of cytokines (IFN-gamma and IL-10) from the spleen of immunized mice stimulated by antigens. Splenocytes were cultured in RPMI 1640 with 10% fetal calf serum and induced with 1 µg/ml antigen (GST-den, GST-AHHC, GST-RHHC, GST-RPHC, ApoB100 peptide, C5aR peptide, PAR-1 peptide, respectively) for 48 hour. Then IL10 and IFN-γ in supernatant of cultured cell were measured with DuoSet mouse IL-10 kit and mouse IFN-γ Quantikine immunoassay kit (R&D system, Minneapolis) according to manufactory's protocol.

FIGS. 8A & 8B show the investigation of antigen-specific regulatory function in antigen-immunized mice. Inhibition of CD4$^+$CD25$^-$ effector T cell proliferation by CD4$^+$CD25$^+$ regulatory T-cells isolated from the spleen of control (GST-den-immunized) and construct-immunized mice when AHHC, RHHC and RPHC were used as antigens.

FIG. 8A: Quantitative analyses of proliferation of CD4$^+$ CD25$^-$ effector T cells in the presence of Treg cell by flow cytometry is shown.

FIG. 8B: Proliferation of effector cells isolated from immunized mice alone is indicated in the leftmost bar of each group. Addition of Treg cells to T effector cells at different ratios was also shown. Data are given as mean of 3 analyses±SEM.

FIGS. 9A-9E show the evaluation of expression of smooth muscle alpha actins, vascular cell adhesion molecule (VCAM)-1 and matrix metalloproteinase 9 (MMP9) in lesion site. FIG. 9A: Photomicrographs showing IHC staining for smooth muscle alpha actin (red), vascular cell adhesion molecule VCAM-1 (green) (scale bar: 100 µm and 12.5 µm for magnified ones). FIG. 9B and 9C: Scatter plot showing means of anti-SMC stained area (FIG. 9B) and anti-VCAM-1 stained area (FIG. 9C) (N=6). FIG. 9D: Photomicrographs showing IHC staining for MMP9 (green) (scale bar: 100 µm and 12.5 µm for magnified ones). FIG. 9E Scatter plot showing means of anti-MMP9 stained area (N=6).

FIG. 10A shows representative photomicrographs showing immunohistochemical staining of the aortic root showed anti-ApoB antibody stained areas (red) in the lesion. (FIG. 10B) Quantitative analysis of ApoB expression in lesions. (FIG. 10C) Representative photomicrographs showing immunohistochemical staining of the aortic root showed anti-HSP60 antibody stained areas (red) in the lesion. (FIG. 10D) Quantitative analysis of HSp60 expression in lesions. Scale bar: 150 µm (unenlarged) and 25 µm (enlarged). N=6 mice. NS: not significant.

FIG. 11A-11F show the evaluation of monocyte differentiation into macrophages.

FIG. 11A and 11B: PBMCs differentiation stimulated by recombinant constructs (1 µg/ml) as assessed by analyses of CD206 expression by flow cytometry and inhibition of differentiation in the presence of respective construct-induced antibodies.

FIG. 11C and 11D: Inhibition of differentiation by respective and other construct induced antibodies.

FIG. 11E and 11F: Individual peptide as a stimulator (1 µg/ml) of monocyte differentiation as analysed by CD206 expression. Data are expressed as average values of 3 analyses.

FIG. 12A-12D show the evaluation of the content of TLR4 and MyD88 contents at the lesion sites. FIG. 12A: Photomicrographs showing IHC staining for TLR4 (red) (scale bar: 100 µm and 12.5 µm for magnified ones). FIG. 12B: Scatter plot showing means of anti-TLR4-stained area (N=6). FIG. 12C: Photomicrographs showing IHC staining for MyD88 (red) (scale bar: 100 µm and 12.5 µm for magnified ones). FIG. 12D: Scatter plot showing means of anti-MyD88-stained area (N=6).

FIGS. 13A & 13B show (FIG. 13A) Representative photomicrographs showing immunohisto-chemical staining of the aortic root showed anti-CD11c antibody stained areas (green) overlapped with anti-TLR4 antibody stained area (red) in the lesion (yellow). (FIG. 13B) Measurement of combined area of CD11c and TLR4) occupied in lesion (%). Scale bar: 141 µm (unenlarged) and 26 µm (enlarged).

FIGS. 13C shows the statistical analysis of the effect of immunization with the peptides.

FIG. 14A shows the SEQ ID NO:1 of the native dendroaspin amino acid sequence, FIG. 14B shows the amino acid sequence of C5a SEQ ID NO:2 and FIG. 14C shows the amino acid sequence of C5Ar SEQ ID NO:6.

DETAILED DESCRIPTION

Figure 2A:
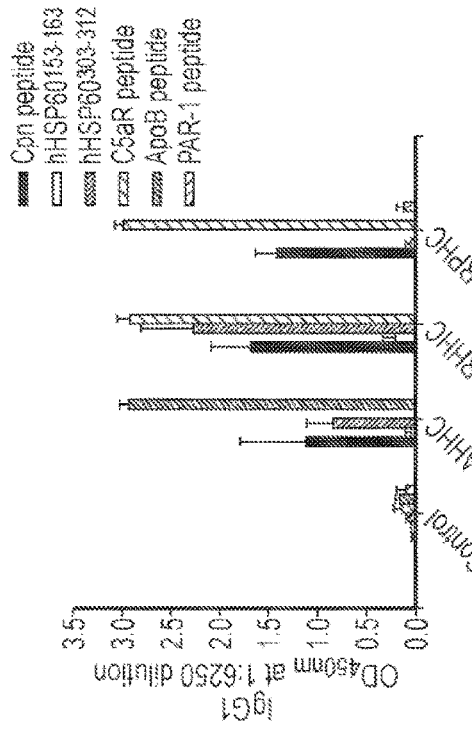

Data indicates that the C5a/C5aR pathway towards atherosclerosis is independent from that of PAR-1/HSP/Cpn pathway based on studies of immunized Apob$^{tm2Sgy}$Ldlr$^{tm1Her/J}$ mice. The present invention provides products and vaccines for targeting both pathways simultaneously using combined epitopes within a dendroaspin scaffold.

Our previous study demonstrated that construct AHHC [ApoB100$^{688-707}$+hHSP60$^{303-312}$+hHSP60$^{153-163}$+Cpn derived peptide (C)] significantly reduced atherosclerotic lesion (Lu et al Atherosclerosis 2012, 225: 56-68). The present invention provides modulations and derivatives of this construct with a sequential epitope-substitution named RHHC in which A was replaced by an "R" (C5aR$^{1-31}$) and RPHC with a further "H" (hHSP60$^{303-312}$) conversion into "P" (protease-activated receptor-1$^{42-55}$) in mice. An alternative embodiment is the construct AH$^h$H$^m$R wherein the antigenic epitopes are from ApoB (AA688-707), designated as A, human HSP60 (AA303-312) (SEQ ID NO: 12) designated as H$^h$, mycobacterium (AA253-268) (SEQ ID NO:15) designated as H$^m$ and complement component 5a receptor (AA1-31) (SEQ ID NO:9) designated as R. Immunization of B6;129S-Ldelr$^{tm1Her}$Apob$^{tm2Sgy}$/J mice with these elicited production of high levels of antibodies against each epitope (apart from hHSP60$^{153-163}$ and P which induced a low antibody response). Histological analyses demonstrated that the mice immunized with either RPHC or RHHC showed significant reductions in the size of atherosclerostic lesions compared to those with AHHC (69.5±1.1% versus 55.7±3.4%, P=0.006 or 65.6±1.3% versus 55.7±3.4%, P=0.045). Reduction of plaque size in the aortic sinus and descending aorta correlated with alterations in cellular immune responses when compared with controls.

We conclude that these new recombinant constructs may provide new antigenic and structural features which are favourable for significant reduction in atherosclerotic lesion formation. This present invention offers a novel strategy for developing anti-atherosclerotic agents.

Based on the effects of the peptides derived from C5aR and PAR-1 on reducing the atherosclerotic lesion, we hypothesized that the effect of a multi-epitopic construct on reducing atherosclerotic lesion may be modulated towards favorable plaque phenotype and increased lesion reduction with inclusion of C5aR and PAR-1 in vaccination. In the present study we investigated the effect of C5aR and PAR-1 including constructs through a sequential substitution: AHHC→RHHC (R denotes an epitope derived from C5aR) in RHHC→RPHC (P denotes an epitope derived from PAR-1) on reducing atherosclerotic lesion. The induced immune response is associated with an anti-atherogenic effect, detected as a significant reduction in the size of the atheromatous lesion area both in aorta sinus and descending aortas with a rate in the following order: RPHC≥RHHC>AHHC.

Native dendroaspin is a 59 amino acid peptide and the dendroaspin scaffold lends itself to modification. When dendroaspin (including the RGD motif) is modified to incorporate further functional amino acid sequences e.g. active portions or motifs of agonists, antagonists or inhibitors of factors in the clotting cascade, the resulting molecules are particularly useful as anticoagulants and do not suffer from the drawbacks associated with existing anticoagulants (see International application WO 01/57210). Such hybrid polypeptides may comprise a first amino acid sequence including the RGD motif and conferring dendroaspin activity and a further amino acid sequence conferring activity other than that of dendroaspin activity. In this way the hybrid dendroaspin-based molecules molecules may be rendered multifunctional.

C5a is a protein fragment released from complement component C5. This 74 amino acid peptide in humans is generated by the cleavage of C5a convertase on the C5 $\alpha$-chain during the classical, alternative, and lectin pathways of complement activation.

The C5a receptor also known as component 5a receptor (C5AR1) or CD88 (cluster of differentiation 88) is a G protein-coupled receptor for Ca. Human C5aR is an integral membrane glycoprotein consisting of 350 amino acids forming a single poly-peptide chain. The C5aR is not released as a soluble receptor and does not circulate. C5aR is expressed on differentiated myeloid cells, such as U937 and HL-60. C5aR is expressed on liver parenchymal cells, lung vascular smooth muscle, lung and umbilical vascular endothelial cells, bronchial and alveolar epithelial cells, HepG2 cells, a hepatoma cell line, mesangial cells, as well as astrocytes and microglial cells, on cultured human fetal astrocytes and astrocyte cell line.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

Expression and Purification of Recombinant Glutathione S-Transferase Constructs

Glutathione S-transferase-dendroaspin (GST-tagged-den here referred to as a control, FIG. 1A) and GST-recombinant construct AHHC [ApoB100 peptide, amino acids (aa) 688-707 (numbered including signal peptide), human heat shock protein (hHSP) 60 peptide, aa 303-312 and aa153-163, respectively; and *Chlamydia pneumoniae* (Cpn) derived epitope ("C", denotes a combination of aa 66-73 from major out membrane protein (MOMP) and aa 283-291 from outer membrane 5 of Cpn)] was described previously and construct RHHC ("R" denotes a C5aR peptide, aa 1-31) and RPHC ("P" denotes an protease activated receptor-1 (PAR-1) peptide, aa 42-55) were generated. Schematic presentation of these constructs using dendroaspin as a scaffold is shown in FIG. 1B. These recombinant molecules were expressed in *Escherichia coli* (BL-21 strain), purified by affinity and ion exchange chromatography and analyzed by sodium dodecyl sulfate polyacrylamide gel electrophoresis, all these procedures were similar to those described for AHHC previously [Lu et at 2012; Atherosclerosis 225: 56-68].

Animal Experiments

B6;129S-Ldelr$^{tm1Her}$Apob$^{tm2Sgy}$/J mice were used, each group of mice consisting of 5-6-week-old males. Dendroaspin as a control antigen, since dendroaspin was used as a scaffold and previous data showed no effect of dendroaspin on lesion reduction when used for subcutaneous immunization in mice.

The immunizing antigens used were constructs AHHC, RHHC and RPHC, respectively. The repetitive immunization multiple sites strategy (RIMMS) was adopted [1] and mice were sacrificed at the end of week 12 (a high-fat diet was started at the end of week 2 and continued for 10 weeks). The control groups followed the diet program after immunization with GST-tagged Den and Alum (adjuvant).

Tissue Preparation and Antibody Response Measurements

Twelve weeks after the first immunization, aorta tissues were harvested and mounted in optimal cutting temperature compound (OCT) and in paraffin, for immunohistochemical (IHC) analyses and lesion measurement, respectively. Atherosclerotic lesions in aortic roots were examined by an Olympus UULH Optical microscope (Olympus Optical Co. Ltd, Tokyo, Japan) and analyzed with Image-Pro Plus™ software, version 7.0 (Media Cybernetics, Inc., Bethesda, Md., USA). Longitudinally opened descending aortas were evaluated for the extent of atherosclerosis after Oil Red O (ORO) staining. The peptide-specific antibody levels in the plasma samples were measured by ELISA following the manufacturer's instructions. One third of spleens were embedded in OCT and the remaining part was homogenized by pressing through 70 μm cell strainer and frozen for further analysis.

IHC and Morphometric Analyses, Quantitative Measurements of Atherosclerosis, and IHC Analysis of Forkhead Box Protein 3 (Foxp3) Expression in CD4+ Splenocytes.

OCT-embedded samples were used for detection of CD68, CD11c, Interleukin (IL)-10 and tumour necrosis factor (TNF)-α, Foxp3, vascular cell adhesion molecule (VCAM)1, alpha smooth muscle cell (alpha-SMC), matrix metalloproteinase 9 (MMP9) by IHC analyses. Sections of paraffin-embedded tissues were stained with hematoxylin and eosin (HE) and elastin/van Gieson (Sigma) for histological examination by the Olympus U-ULH Optical microscope.

Flow Cytometric Analysis of Foxp3, IL-2, IL-4 and IL-17A Expression in CD4+ T-Cells in Splenocytes and Differentiation of PBMC into Macrophage (CD206).

Spleen cells were processed for staining (30 min at 4° C.) using allophycocyanin-anti-mouse Foxp3, IL-2, IL4 and IL-17 antibodies (BioLegend, Cambridge, UK). For cell differentiation assay, mouse (C57BL/6) PBMCs were stimulated with different antigens or pre-incubated with antiserum of antigen (in order to see any antagonism of antiserum). Antigen-induced differentiation of monocytes into macrophages was measured by flow cytometry which was compared to cell populations from non-induced cells or control antigen (GST-Den)-induced cells.

Measurement of Cytokines

IL-10 and TNF-α levels in the lesions were quantified by IHC analyses (rat anti-mouse TNF-α and IL-10 purchased from BioLegend, CA, USA). Plasma levels of the cytokines, IL-10, transforming growth factor beta (TGF-β), TNF-α and interferon gamma (IFN-γ) were measured by ELISA following the manufacturer's instructions (R&D systems, Abingdon, UK). Levels of concanavalin A (ConA)-induced IL-10, TGF-β, TNF-α, and IFN-γ in splenocyte cultures were also measured.

Antigen-Specific Regulatory T Cell Function Assays

To assess antigen-specific regulatory T cell function, CD4+CD25+ Treg cells were isolated by using regulatory T cell isolation kit of Miltenyi Biotec (Bergisch Gladbach, Germany) from spleen CD4+ T cells of B6;129S-Ldelr$^{tm1Her}$Apob$^{tm2Sgy}$/J mice immunized subcutaneously with constructs, respectively. CD4+CD25− T effector cells were isolated from spleen CD4+ T cells (unbound to beads binding CD4+CD25+ cells, 99.5% of CD4+ cells) of same construct-immunized mice respectively. CD4+CD25− cells (2×10$^5$) were co-cultured with CD4+CD25+ cells (2×10$^5$), and stimulated with 1 μM related construct or with GST-Den control. After 2 days of culture, the proliferation of T effector cells was measured for the shift in fluorescence intensity of a population of cells by flow cytometry expressed as mean fluorescence intensity (MFI).

Statistical Analyses

Data are reported as mean±standard error of the mean (±SEM), unless otherwise indicated. Figures were plotted using graph-pad Prism 5.01 and Sigma plot 9.0. For atherosclerotic lesion size, data were compared and intergroup differences were analyzed using one-way ANOVA for multiple comparisons and post hoc Bonferroni test. Other data were analyzed using Student's t-test (2-tailed analyses). Non-parametric distributions were analyzed using the Mann-Whitney U test for pair wise comparisons and the Kruskal-Wallis test for multiple comparisons. Differences between groups were considered significant at P values below 0.05.

Example 1

Peptide-specific immunoglobulin G in the sera of immunized mice was assessed. Antibody levels were measured by ELISA test in the sera of mice immunized with either dendroaspin (GST-tagged) or constructs within dendroaspin scaffold (GST-tagged) at weeks 2 and week 12 respectively after first immunization. In AHHC-immunized mice, ApoB peptide-, hHSP60$^{303-312}$- and Cpn-peptide-specific antibodies were observed when these peptides were used as ELISA antigens (FIG. 2A). Similarly C5aR peptide-specific antibodies were detected in addition to observed hHSP60$^{303-312}$- and Cpn peptide-specific antibodies in mice immunized with RHHC (FIG. 2A). High antibody levels against Cpn peptide and C5aR peptide whereas low antibody level against PAR-1 peptide was detected in mice immunized with RPHC (FIG. 2A). Low antibody level against hHSP60$^{153-163}$ was observed in mice immunized with any construct (FIG. 2A). Overall observed optical density (OD) values at 100 dilutions were reduced at week 12 compared to those at week 2.

Figure 2B:
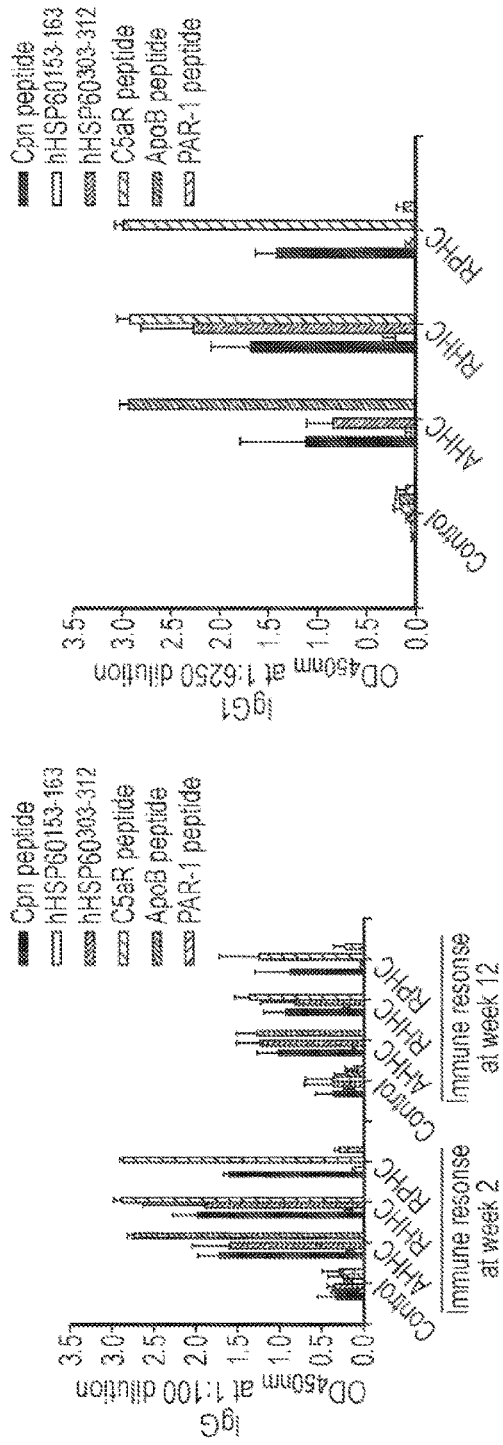
Figure 2C:
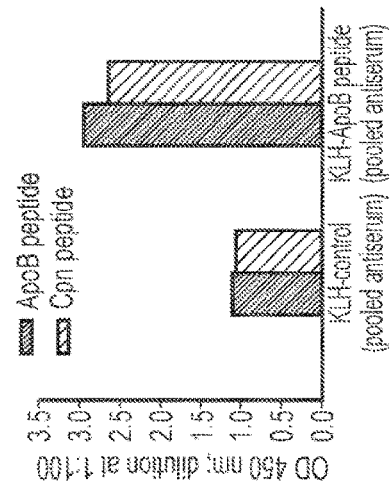
Figure 2D:
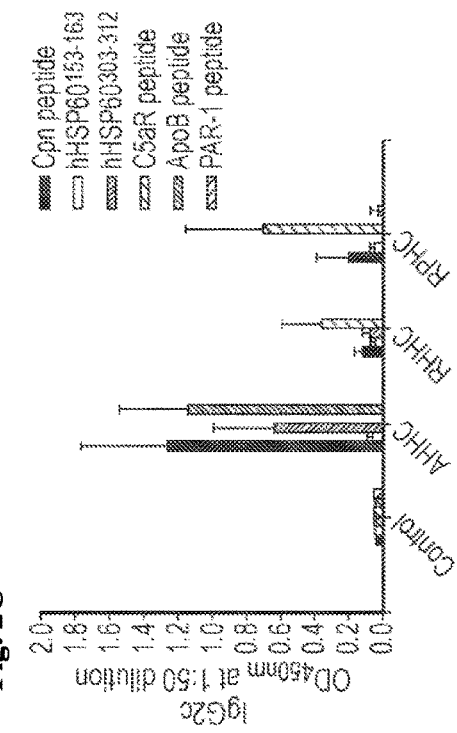

Interestingly, a peptide-induced specific immunoglobulin (Ig)G1 response was observed in serum of peptide-immunized mice against all peptide antigen epitopes at high dilutions except for those against hHSP60$^{153-163}$ and PAR-1 peptides when compared with GST-Den control (FIG. 2B). In addition, a similar pattern for IgG2c response was also detected but with low serum dilutions when compared with that in control (FIG. 2C). However, the levels of IgG2c detected were much lower than those of IgG1 based on the optical densities measured in different dilutions of samples (1:50 versus 1:6250). Furthermore, using antiserum at week 8, certain levels of cross-reactions were observed between ApoB peptide-induced antiserum and Cpn peptide (FIG. 2D), between ApoB peptide- and hHSP60$^{303-312}$ peptide-induced antiserum and their antigens (FIG. 2E), between ApoB peptide-induced antiserum and antigens of either PAR-1 peptide or C5aR peptide (FIG. 2F) and between C5aR peptide-induced antiserum and antigens of either ApoB peptide or PAR-1 peptide (FIG. 2G). Apart from cross-reaction between Cpn peptide and ApoB peptide antiserum when pooled sera were tested and thus no SD values were calculated (FIG. 2D), the other cross-reactions showed significant difference compared to the controls (FIGS. 2E-G; P<0.05~<0.001).

Example 2

The reduction of atherosclerotic lesion size in the aortic sinus was assessed. Following immunization with AHHC, RHHC, RPHC, and after a 10-week high-fat diet, the aortic sinuses of the mice were evaluated for the extent of atherosclerosis. The calculated plaque sizes from the immunized animals were compared with those of the controls.

Representative photomicrograph of sections with lesions from experimental groups are shown in FIG. 3A. The plaque areas are shown in FIG. 3B. Lesion size was smaller in mice immunized with all three constructs showing 31,071±998.7 μm$^2$, 24,123±1967 μm$^2$ and 21,386±2482 μm$^2$ (P<0.001) compared with controls (70200±5718 μm$^2$). The smaller lesion area was observed in mice immunized with either RHHC or RPHC compared with mice immunized with AHHC (P=0.007-0.002) (FIG. 2B). The percentage of reduction in lesion size is shown in FIG. 3C, showing 55.7±3.4%, 65.6±1.3% and 69.5±1.1% when assuming reduction in lesion of control animals as zero percent. The control mice that were immunized with GST-Den showed similar lesion formation in either GST-tag- or Alum (adjuvant)-immunized controls (FIGS. 4A and 4B). Therefore, GST-Den was used as a control throughout the experiment.

The impact of treatment with these recombinant constructs on the collagen content in these lesions was also examined. The reduction of atherosclerosis in mice treated with these constructs was associated with an increase in collagen content: approximately 3-fold for either AHHC-immunized mice or RHHC-immunized mice versus control mice (18.6±1.2% or 19.4±0.9% versus control 5.9±0.3%; P<0.001), respectively (FIGS. 3D and 3E). Mice immunized with in RPHC showed a significant collagen increase (24.4±0.9%) compared with mice immunized with either AHHC or RHHC (P=0.003, and P=0.007, respectively).

Longitudinally opened descending aortas were stained en face with oil red 0 (ORO) and positively stained plaques areas were measured. Representative en face stained descending aortas from experimental groups are shown in FIG. 3F. Lesion size was significantly smaller in mice immunized with any construct showing 8.4±0.3%, 6.6±0.3% and 6.4±0.4% for AHHC, RHHC, and RPHC, respectively compared with controls (19.5±1.7%, P<0.001) (FIG. 3G). Both RHHC- and RPHC-immunized mice showed significantly less lesion than AHHC-immunized mice (P=0.011-0.008). The reduction of lesions expressed as a percentage is shown in FIG. 2H with 57.3±1.7%, 66.1±1.6% and 67.3±1.9% for AHHC, RHHC, RPHC, respectively. The smallest lesion area was observed in mice immunized with RPHC.

Example 3

Figure 5A:
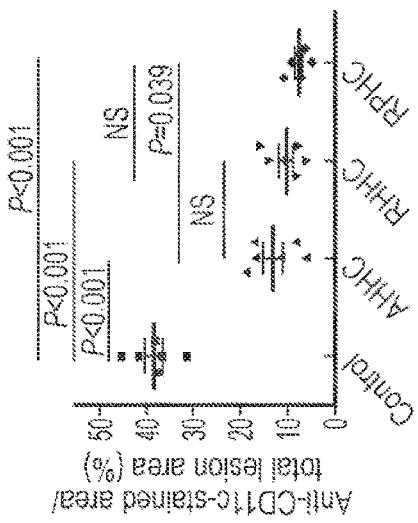
Figure 5B:
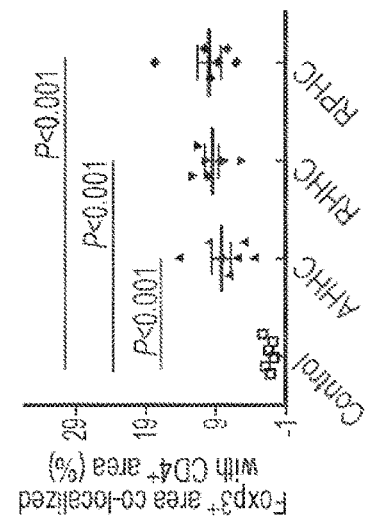
Figure 5C:
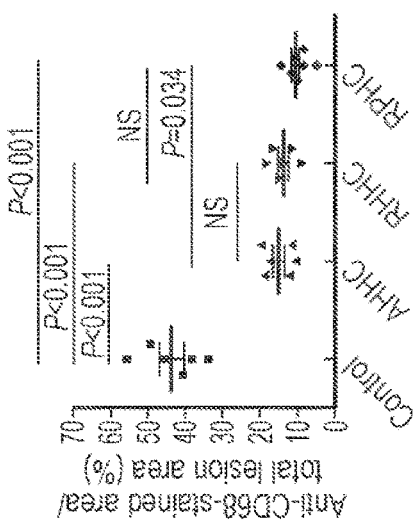
Figure 5D:
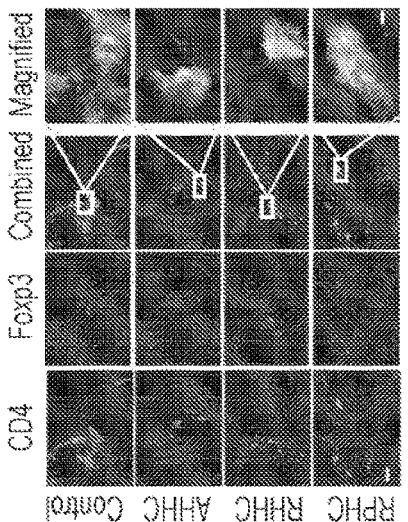
Figure 5E:
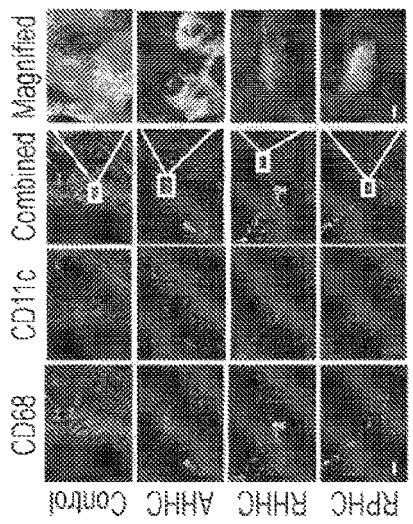
Figure 5F:
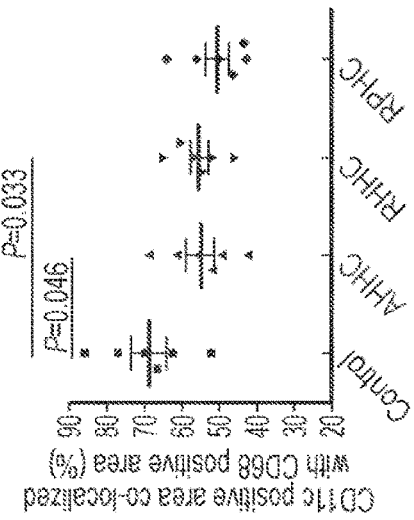

The amount of inflammatory cells and CD4$^+$ T cells expressing Foxp3 in local (lesions of aortas) and remote organs: splenocytes and lymphocytes was assessed. The percentage of anti-CD68-stained area in the lesions showed 14.9±1.6%, 13.6±1.3% and 10.3±0.8% in mice immunized with AHHC, RHHC and RPHC, respectively compared to 43.7±3.2% in control mice immunized with GST-Den (P<0.001). Lesser anti-CD68-stained area was observed in RPHC-immunized mice compared with that in AHHC-immunized mice (P=0.034) (FIGS. 5A and 5B). Similarly, measurement of anti-CD11c-stained lesion area showed 13.3±2.1%, 10.5±1.5% and 7.9±0.8% in mice immunized with AHHC, RHHC and RPHC, respectively compared to 38.4±1.9% in control mice (P<0.001) (FIGS. 5A and 5C). Anti-CD11c-stained lesion area in RPHC-immunized mice was significantly smaller when compared with that in AHHC-immunized mice (P=0.039) (FIGS. 5A and 5C). Double immunostaining for CD68 and CD11c clearly revealed that more than half of macrophages were CD68$^+$ CD11c$^+$, indicating the myeloid origin of this cell type in lesions as CD11c$^+$ area co-localized with CD68$^+$ area expressed as percentage showing 54.7±3.7%, 55.2±2.6% and 50.3±3.3% for AHHC, RHHC and RPHC, respectively compared to 68.6±4.7% in control mice (FIGS. 5A-5D; P=0.046-0.011). The proportion of CD4$^+$ cells expressing Foxp3 analyzed by IHC staining of aorta sections was approximately 6- to 8-fold higher (8.2±1.4%, P<0.001; 9.4±1.1%, P<0.001; 9.9±1.6%, P<0.001) in mice immunized with AHHC, RHHC and RPHC, respectively compared to 1.2±0.2% in control mice (P<0.001) (FIGS. 5E and 5F). In addition, expression of Foxp3 in CD4$^+$ spleen cells from mice immunized with these three constructs was higher (P<0.001) than that in controls, showing 13.3±0.6%, 15.3±1.5%, and 18.0±1.1%, for AHHC, RHHC and RPHC respectively versus 4.0±0.5% in controls (FIGS. 5G and 5H). With the exception of RPHC-immunized mice, which did not show a significant increase of Foxp3 expression when compared with that in RHHC-immunized mice, however, significantly higher levels of Foxp3 expression were observed in comparison with that in AHHC-immunized mice (P=0.002).

Example 4

Figure 6I:
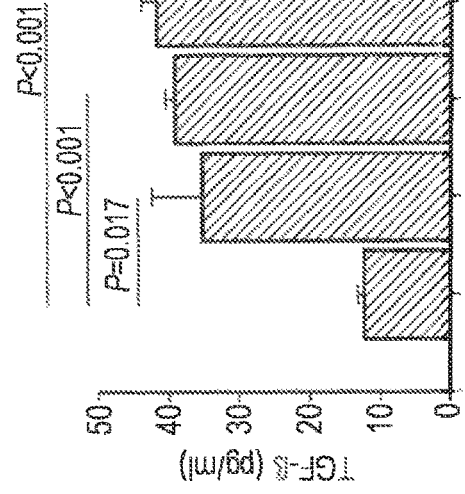
FIG. 6I-L: Cytokine levels measured in the supernatant of splenocytes stimulated with ConA.

The expression of anti-inflammatory cytokines and proinflammatory cytokines in lesion sites and levels of cytokines in plasma and in the supernatants of stimulated splenocytes was assessed. IL-10 expression in the aortic lesions of mice immunized with AHHC, RHHC and RPHC, detected by IHC analyses is shown in FIG. 6A. The proportion of CD4$^+$ cells expressing IL-10 in the lesions was approximately 6-fold higher in mice immunized with these constructs, showing 4.8±0.7%, 5.2±0.8% and 5.9±0.7% (P<0.001) for AHHC, RHHC and RPHC, respectively when compared with that in the control group (0.9±0.2%) as shown in FIGS. 6A and 6B. IHC analyses of TNF-α expression showed significantly smaller TNF-α-occupied areas in lesions of mice immunized with constructs compared with controls (25.7±3.1% for AHHC; 15.2±0.9% for RHHC; 15.5±1.5% for RPHC and 41.3±3.1% for controls) (FIGS. 6C and 6D). These data represent a percent reduction of 37.8%, 63.2%, and 62.5%, respectively, compared with controls (total lesion area defined as 100%, and 0% reduction). Additionally, enhanced reduction was produced by either RHHC or RPHC versus AHHC (P=0.008-0.014).

Plasma levels of atheroprotective cytokines IL-10 were significantly increased in mice immunized with these three constructs compared with controls (FIGS. 6E and 6F). Immunization with RPHC had more effect than with other two constructs on promoting the secretion of IL-10 and TGF-β (P<0.05 to <0.001). Plasma levels of the atherogenic cytokine TNF-α were significantly reduced by immunization with these three constructs (FIG. 6G). A similar trend was obtained for these constructs in respect of plasma levels of IFN-γ (FIG. 6H). Notably, immunization with RPHC had more effect than with AHHC on reducing the secretion of TNF-α and IFN-γ (P≤0.002) and more effect than with RHHC on reducing the secretion of TNF-α (P=0.004). Although slightly higher plasma levels of IFN-γ from mice immunized with AHHC was observed compared to that of control mice (24 versus 20.8 pg/ml), this difference did not show statistical significance.

Figure 6J:
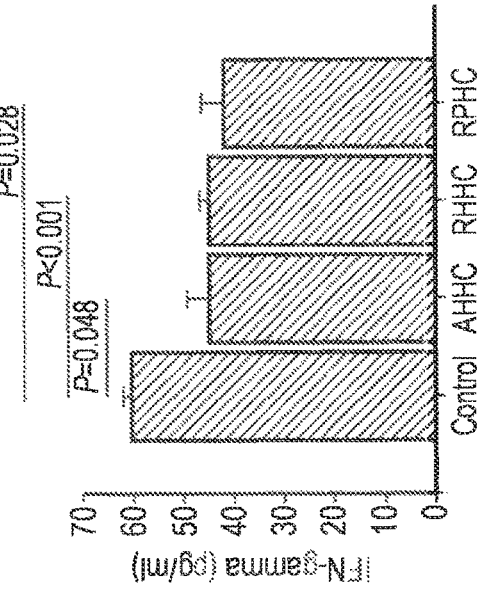
Figure 6K:
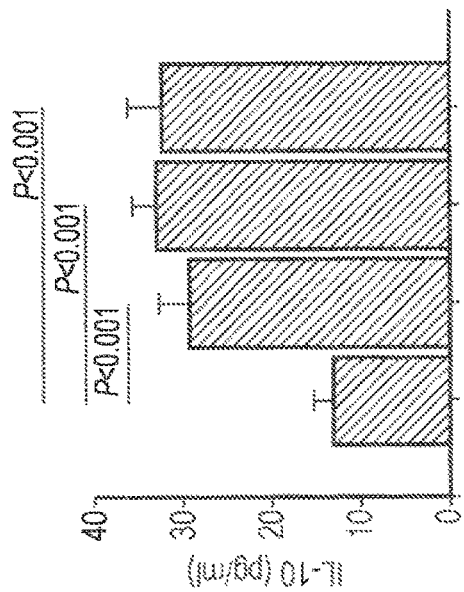
Figure 6L:
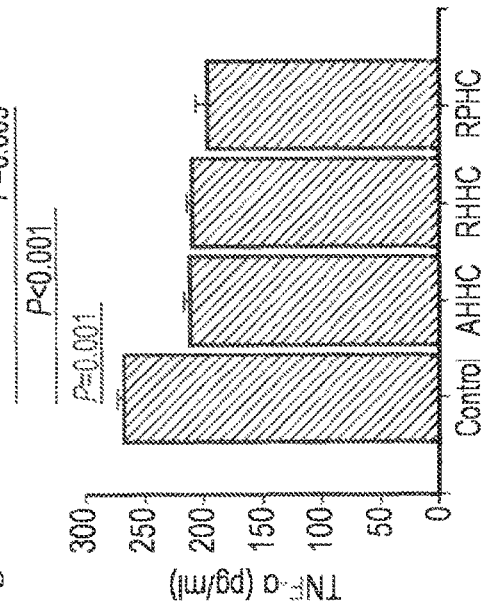

Supernatants of splenocytes from mice immunized with these constructs individually showed significantly increased secretion of IL-10 (FIG. 6I) and TGF-β (FIG. 6J), stimulated with 10 µg/mL of ConA (P<0.05-0.001) when compared to those of controls. In addition, higher levels of either IL-10 or TGF-β were produced by splenocytes of RPHC-immunized mice than those of AHHC-immunized mice (P<0.05-0.01). In contrast, TNF-α (FIG. 4K) and IFN-γ levels (FIG. 6L) were significantly decreased in the supernatants of splenocytes of mice immunized with these constructs compared with the control when stimulated with 10 µg/mL of ConA. Notably, levels of TNF-α and IFN-γ in RPHC-immunized mice were lower than those in AHHC-immunized mice (P<0.05-0.01) when stimulated with 10 µg/mL of ConA, respectively. Interestingly, supernatants of splenocytes from mice immunized were also shown to contain increased amount of protective cytokine IL-10 and decreased amount of proinflammatory cytokine IFN-γ when stimulated with either peptides or construct containing peptides but not in the case when stimulation was done with KLH, a different protein (FIGS. 7A-D). In most cases, the changes in cytokine productions in response to different stimulators were significant except for the cases when ApoB, C5aR and Cpn peptides were used as stimulators for the production of IL-10 in GST-den-immunized mice, and PAR-1 peptide in RPHC-immunized mice.

Figure 6Q:
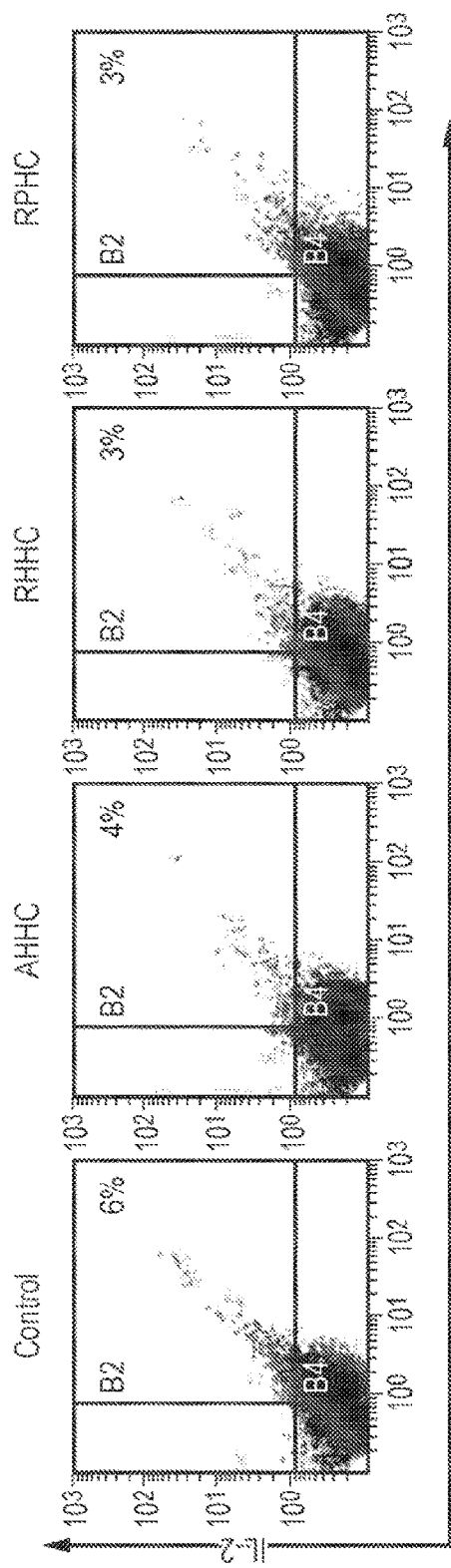
FIG. 6Q: Representative analysis of CD4+IL-2$^+$ T-cells in splenocytes from construct-immunized mice fed on a high-fat diet as assessed by flow cytometer.
Figure 6R:
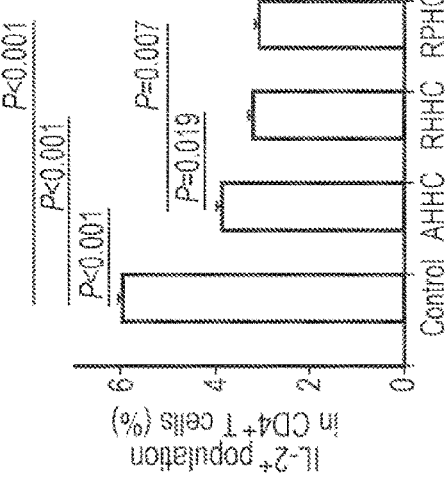

The proportion of IL-4 (Th2-related), IL-17A (Th17 related) and IL-2 (Th1-related) expressing CD4$^+$ spleen cells from mice immunized with these three constructs was significantly lower (P<0.001 for IL-4$^+$ and P≤0.001 for IL-17A$^+$, respectively), showing 2.74±0.11% (AHHC), 2.85±0.12% (RHHC), and 2.87±0.02% (RPHC) for IL-4$^+$ when compared to 8.44±0.21% (control) (FIGS. 4M and 4N); 2.0±0.1% (AHHC), 1.7±0.1% (RHHC), and 0.9±0.1% (RPHC) for IL-17A$^+$ when compared to 4.1±0.3% (control) (FIGS. 6O and 6P). In addition, smaller percentage of CD4+IL-17A$^+$ expressing spleen cells was observed in RPHC-immunized mice compared to that in either AHHC- or RHHC-immunized mice (P≤0.006) (FIGS. 6O-P). Interestingly, higher percentage of CD4$^+$IL-17A$^+$ expressing spleen cells was observed in RHHC-immunized mice compared to that in RPHC-immunized mice (P=0.021) (FIG. 6P). Furthermore, significantly lower percentage of CD4$^+$IL-2$^+$ expressing spleen cells was observed in three construct-immunized mice when compared to that in control (P<0.001; FIGS. 6Q and 6R). Additionally smaller percentage of CD4$^+$IL-2$^+$ expressing spleen cells was observed in RPHC-immunized mice compared to that in either AHHC- or RHHC-immunized mice (P=0.019-0.007).

Example 5

Antigen-induced specific Treg cell function was investigated. To assess whether functional Treg cells were induced by immunization, antigen-specific Treg cells (CD4$^+$CD25$^+$ T cells) were co-cultured with CD4$^+$ effector T-cells (CD4$^+$ CD25$^-$ T cells). Proliferation of effector T-cells from control mice immunized with GST-Den in response to stimulation with GST-Den at 1 μM did not show suppression in the presence of Treg cells from GST-Den-immunized mice (FIGS. 8A and 8B). In contrast, proliferation of effector T cells from sampling mice immunized with AHHC, RHHC and RPHC in response to stimulation with related antigen respectively was inhibited (FIGS. 8A and 8B), when CD4$^+$ CD25$^-$ effector T cells were co-cultured with CD4$^+$CD25$^+$ Treg cells isolated from these mice. The differences were significant when Treg cells were added to the effector cells at the ratios between 4:1-16:1 (P<0.05~<0.001) compared with that without the addition of Treg cells.

Example 6

An evaluation of expression of smooth muscle alpha actins, VCAM1, MMP9 and specific antigens ApoB and HSP60 in the lesions was undertaken. To assess whether immunization with the constructs of the present invention influences vascular SMC behavior and vascular remodeling, the SMC content of lesions and expression of VCAM1 and MMP9 at lesion sites was analysed by IHC analyses. Anti-SMC stained area was significantly smaller in the plaques of mice immunized with AHHC and RPHC, showing 5.2±0.7% and 4.9±0.8%, respectively, but it was not reduced significantly in mice immunized with RHHC when compared with that in controls immunized with GST-Den (FIGS. 9A and 9B). In addition, expression of VCAM1 was significantly down-regulated, showing 4.5±0.9%, 7.8±0.9%, and 4.8±0.9%, for AHHC, RHHC and RPHC, respectively, compared with that in controls immunized with dendroaspin (18.0±2.3%) (FIGS. 9A and 9C). A significantly increased effect was found in RHHC-immunized mice compared to that in AHHC- or RPHC-immunized mice (FIGS. 9A and 9C). A similar trend was observed for MMP9 expression in mice immunized with all three constructs 7.9±1.0%, 10.1±1.0%, and 7.6±1.0% stained areas were shown in AHHC-, RHHC- and RPHC-immunized mice, respectively, and 18.1±2.5% in control mice immunized with GST-Den (FIGS. 9D and 9E), except for that there is no significant difference obtained in this respect between either AHHC- or RPHC-immunized mice and RHHC-immunized mice (FIGS. 6D and 6E). Interestingly, the injection of recombinant construct containing human ApoB and HSP60 peptides did not affect the expression of their counterparts (ApoB and HSP60) as little difference of mouse ApoB (FIGS. 10A and 10B) and mouse HSP60 protein (FIGS. 10C and 10D) antigens was detected at the lesion sites between sampling and control mice.

Example 7

Figure 11E:
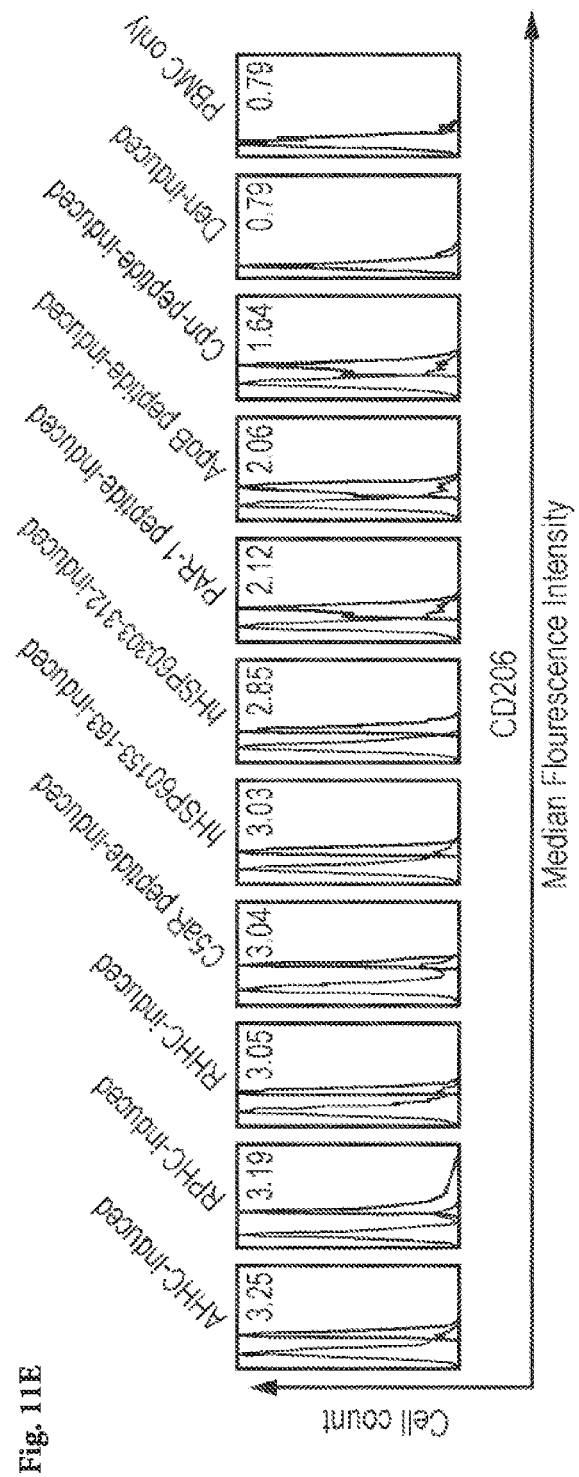
Figure 11F:
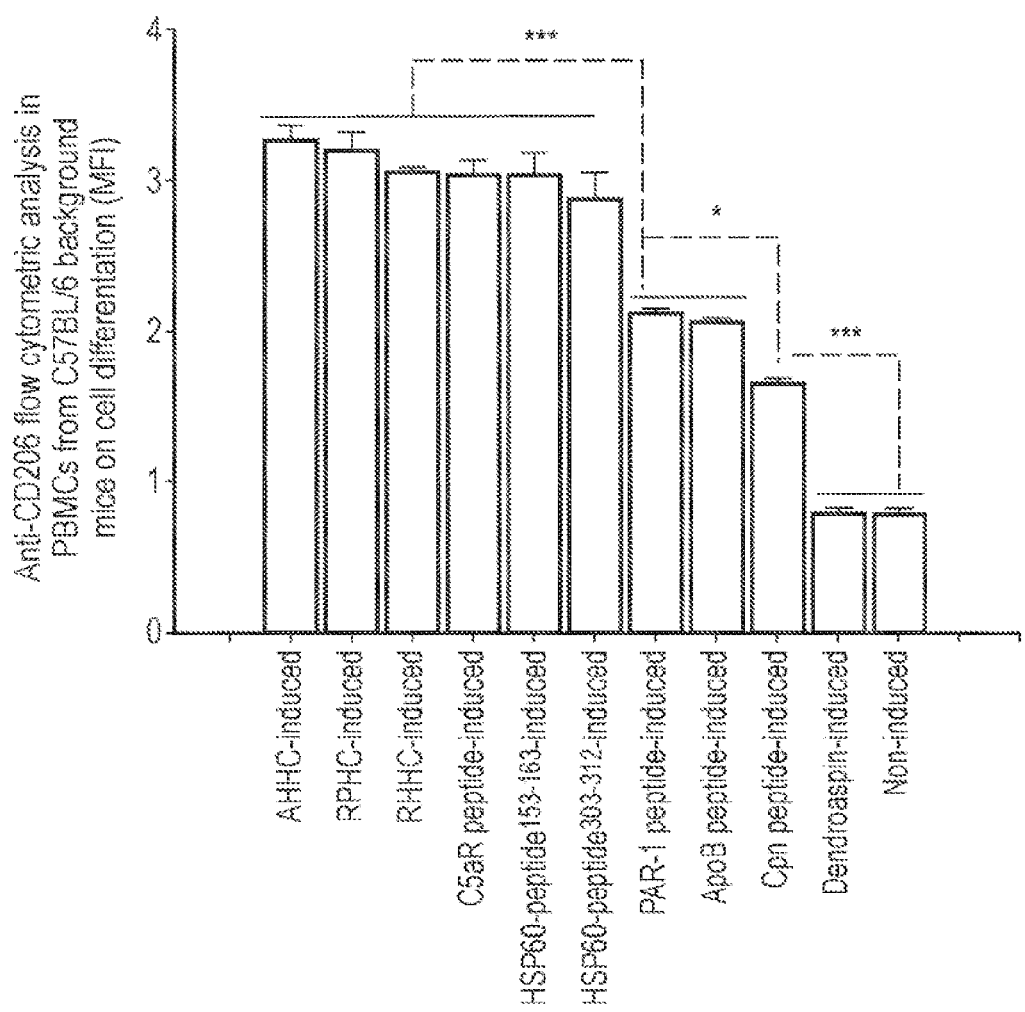

Evaluation of monocyte differentiation into macrophages in PBMC from C57BL/6 background naive mice in response to treatment with recombinant constructs and the effect of construct-specific immune sera on the differentiation was investigated. In vitro, monocytes can differentiate into macrophage (or subsets) upon stimulation with macrophage-colony stimulating factor (M-CSF) or atherogenic antigens. To assess whether AHHC converted into RHHC with a single domain substitution could maintain the same effect on stimulation of monocyte (from naive mice C57BL/6 with same background), PBMCs were stimulated with either RHHC or AHHC. After 3 days, the expression of cell surface marker CD206 (mannose receptor, a macrophage marker) was assessed. Both RHHC- and AHHC-induced monocyte differentiation into macrophages (based on the cell number changes) when compared with non-stimulated cells (FIGS. 11A and 11B). In addition, PBMC differentiation induced by these two constructs was abolished by pre-incubation of the cells with antiserum from mice immunized with these two antigens. Interestingly, the inhibition can be achieved by pre-incubation of the cells with antiserum from each other (FIGS. 11A-11D). Observation of differentiations with individual epitope or domain as a stimulator showed different ratio of differentiation (FIGS. 11E-11F).

Example 8

Evaluation of the contents of Toll-like receptor 4(TLR4) and myeloid differentiation factor 88 (MyD88) which are involved in the TLR4 signal pathway related to atherosclerosis at the lesion sites was investigated. The impact of the treatment with these recombinant constructs on TLR4 and MyD88 contents in lesions was examined. The reduction of atherosclerosis in mice treated with these constructs was associated with a decrease in both TLR4 and MyD88 contents. Anti-TLR4 stained area was significantly smaller in the plaques of mice immunized with AHHC, RHHC and RPHC, showing 4.6±1.0%, 3.4±0.5% and 4.2±0.6%, respectively, compared with that in controls immunized with dendroaspin (8.1±1.1%) (FIGS. 12A and 12B). Similarly, anti-MyD88 stained area was significantly smaller in the lesions of mice immunized with these three constructs, showing 9.7±1.2%, 9.6±1.6% and 10.2±1.9%, respectively, compared with that in controls (18.6±2.4%) (FIGS. 12C and 12D). Additionally, overlapping anti-CD11c and anti-TLR4 stained area showed significantly smaller in the lesions of mice immunized with all three constructs, showing 3.4±0.6%, 2.9±0.7% and 2.7±0.8%, respectively, compared with that in controls (6.6±0.8%) (FIGS. 13A and 13B).

Example 9

Experiments were conducted to compare two HSP60 peptides derived from human and *mycobacterium*, respectively, for their ability to reduce atherosclerotic lesions through immunization in $Apob^{tm2Sgy}Ldlr^{tm1Her}$/J Mice. Mice were immunized with two Keyhole limpet hemocyanin (KLH)-conjugated peptides derived from mycobacterial heat shock protein (HSP) 60 (AA253-268) (SEQ ID NO:15) designated as $mHSP60^{253-268}$, human HSP60 (AA516-528) (SEQ ID NO:14) designated as $hHSP60^{516-528}$, respectively. Mice were immunized with these two peptides and two weeks after the first immunization, mice were placed on a high-fat diet. Results indicated that the two peptides showed similar functions apart from that mHSP60 peptide has lower titres for IgG and IgG1 and little for IgG2c, than those of hHSP60 peptide. Similar functions include: induced specific immune responses; lesion reduction; increased Treg expression; increased concentration of atheroprotective cytokines: IL-10 and TGF-β and decreased concentration of pro-inflammatory cytokines: TNF-α and INF-γ; inhibition of $CD4^+CD25^-$ T-cell proliferation by Treg cells and down-regulation of TLR4/MyD88 pathway (data not shown). In conclusion, after immunization of B6; 129S-Ldlrtm1HerApobtm2Sgy/J mice with mHSP60 and hHSP60 peptides, in spite of a low sequence homology (31%) between two peptides and lower immune responses obtained from mHSP60 peptide, both peptides have similar effects on significantly reduced early atherosclerotic lesions. This data confirms that such immunization with the constructs of the present invention offers attractive opportunities for the design and development of peptide-based vaccines against atherosclerosis.

Example 10

The transcriptional regulator FOXP3 (forkhead box P3) governs mouse $CD4^+CD25^+$ Treg function (Fontenot et al., *Nat Immunol.* 2003;4:330-336; Hori S, Nomura T, Sakaguchi S. *Science.* 2003; 299:1057-1061) and it has been shown that transfer of natural $CD4^+CD25^+$ Tregs significantly reduces plaque progression in the ApoE-KO mouse model (Ait-Oufella et al., Nat Med. 2006;12:178-180; Mor et al *Arterioscler Thromb Vasc Biol.* 2007; 27: 893-900). Accordingly it is known that naturally occurring Tregs are capable of influencing the size and composition of atherosclerotic lesions, several reports support the theory that antigen-specific responses may be operable in the evolving atheromatous plaque. We hypothesized that atherogenic antigen-induced Treg may have a specific function on lesion reduction. We conducted experiments to assess the effect of adoptively transferred Treg cells isolated from the blood of antigen-immunized mice on atherosclerotic lesion formation in $B6;129S-Ldelr^{tm1Her}Apob^{tm2Sgy}$/J mice by testing humeral immune response, the effect on atherosclerotic lesion size and local and systemic cellular responses.

The first method, to look at the immune response and adoptive transfer in KO mice, involved incorporating construct $AH^hH^mR$ into a dendroaspin scaffold to generate a recombinant construct. The antigenic epitopes from ApoB (AA688-707) was designated as A, human HSP60 (AA303-312) (SEQ ID NO: 12) designated as $H^h$, *mycobacterium* (AA253-268) (SEQ ID NO:15) designated as $H^m$ and complement component 5a receptor (AA1-31) (SEQ ID NO:9) designated as R. Mice were immunized with $AH^hH^mR$ by RIMM (repetitive, multiple site immunization strategy) protocol. Treg cells were purified from the blood of immunized mice with $AH^hH^mR$ ($Treg^S$) and with dendroaspin ($Treg^C$) respectively). Adoptive transfer was achieved though retro-orbital plexus of the mice.

The second method, to evaluate the effect of Treg cells on atherosclerotic lesion formation, involved adoptive transfer of Treg cells from the blood of AGD-den (Control)- and AHhHmR—immunized mice, respectively. Recipients were from the same strain non-immunized naive mice and were fed with a high-fat diet (HFD) for 10 weeks then sacrificed. Histological and immunohistochemical assessment of lesion development, analysis of cytokine level, assessment of Treg activity and foam cell formation were evaluated.

Data (not shown) indicated that $Treg^s$ isolated from the blood of atherogenic anti-immunized mice, after adoptively being transferred into the vein of a non-immunized mice when compared to Treg from the blood of non-atherogenic antigen-immunized mice showed lesser lesion formation. Transfer of natural $CD4^+CD25^+$ Tregs significantly reduced plaque progression in the ApoE-KO mouse model. In addition to lesser lesion formation they also showed increased collagen content in lesion sites, increased Treg expression in lesion sites, higher concentration of atheroprotective cytokines (IL-10 and TGF-β) and lower concentration of pro-inflammatory cytokines (TNF-α and INF-γ) in plasma. Down-regulation of expression of αSMC and PECAM at the lesion sites was also observed.

These results show that the constructs of the present invention offer attractive opportunities in the cell-based therapy for the treatment of atherosclerosis.

What is claimed is:

1. A recombinant construct comprising:
   (i) a scaffold portion;
   (ii) a first species of epitope capable of eliciting an anti-arteriosclerotic vascular disease response via a first pathway wherein the first species of epitope is a C5a receptor (C5aR) protein selected from the group consisting of SEQ ID NO:6, SEQ ID NO:7, SEQ ID NO:8, and SEQ ID NO:9;
   (iii) a second species of epitope capable of eliciting an anti-arteriosclerotic vascular disease response via a second pathway that is independent from the first pathway and is independently selected from the group consisting of an apolipoprotein (Apo) epitope and a heat-shock protein (HSP) epitope selected from the group consisting of peptide 1 (AA) 153-160: AELKKQSK (SEQ ID NO:10), peptide 1 (AA) 153-163: AELKKQSKPVT (SEQ ID NO:11), peptide 1 (AA) 303-312: PGFGDNRKNQ (SEQ ID NO:12), peptide 2: AA 277-286 PGFGDNRKNQ (SEQ ID NO:13), and peptide (AA) 516-528: KGIIDPTKWRTA (SEQ ID NO:14); and
   iv) a third species of epitope capable of eliciting an anti-arteriosclerotic vascular disease response via a third pathway that is independent from the first pathway and is independently selected from the group consisting of a protease-activated receptor-1 (PAR-1) epitope or a *Mycobacterium bovis* HSP epitope.

2. The construct according to claim 1 comprising a plurality of first and/or second species of epitopes.

3. The construct according to claim 1, wherein the scaffold portion is a dendroaspin scaffold protein as depicted in SEQ ID NO:1; optionally, wherein the first and/or second species of epitope is incorporated into any one or more of the following positions: (a) loop I and/or loop II; (b) loop I and/or loop III; (c) loop II and/or loop III; (d) loop I, loop II and loop III; (e) an N terminus or C terminus of the dendroaspin scaffold.

4. The construct according to claim 1, wherein the epitopes portion of the construct comprises AH$^h$H$^m$R and wherein A is ApoB100$^{688-707}$ (ApoB100 peptide, amino acids 688-707 (numbered including signal peptide)), H$^h$ is SEQ ID NO: 12, H$^m$ is SEQ ID NO: 15 and R is SEQ ID NO: 9.

5. An antigenic composition comprising the construct according to claim 1, optionally wherein the composition comprises an antigenic hydrophobic complex comprising: (i) an isolated microsome optionally wherein it is an inverted microsome or (ii) an MHC protein or (iii) an inverted micelle or (iv) a synthetic product.

6. A pharmaceutical composition comprising the recombinant construct according to claim 1, formulated as an injectable or oral product, optionally wherein the pharmaceutical composition further includes a suitable adjuvant, excipient, diluent and/or carrier.

7. A pharmaceutical composition comprising the recombinant construct according to claim 1.

8. A vaccine comprising the construct according to claim 1.

9. A method of eliciting an anti-atherosclerosis response in a mammal comprising administering to an individual the recombinant construct of claim 1.

10. A method of treating, or reducing
atherosclerosis in an individual comprising administering to said individual the recombinant construct of claim 1.

11. A method of treating an individual with early stage atherosclerosis or an individual identified as at risk of developing atherosclerosis comprising administering to said individual the recombinant construct of claim 1.

12. A method of eliciting an immune response
against epitopes associated with at least two independent pathways associated with atherosclerosis formation, the method comprising:
1. incubating eukaryotic cells with the recombinant construct of claim 1;
2. preparing microsomes from said incubated eukaryotic cells;
3. incorporating said microsomes of (2) with one or more pharmaceutically acceptable constituents to produce an orally or injectable administrable preparation; and
4. administering said preparation to a mammal or human.

13. The recombinant construct according to claim 1 comprising:
a first species of epitope capable of eliciting an anti-arteriosclerotic vascular disease response via a first pathway is a C5a receptor (C5aR) protein selected from the group consisting of SEQ ID NO:6, SEQ ID NO:7, SEQ ID NO:8, and SEQ ID NO:9; and
a second species of epitope capable of eliciting an anti-arteriosclerotic vascular disease response via a second pathway that is independent from the first pathway and is an apolipoprotein (Apo) epitope; and
another second species of epitope capable of eliciting an anti-arteriosclerotic vascular disease response via a second pathway that is independent from the first pathway and is a heat-shock protein (HSP) epitope selected from the group consisting of HSP 60 and a HSP 65, and wherein the HSP 60 is selected from the group consisting of peptide 1 (AA) 153-160: AEL-KKQSK (SEQ ID NO:10), peptide 1 (AA) 153-163: AELKKQSKPVT (SEQ ID NO:11), peptide 1 (AA) 303-312: PGFGDNRKNQ (SEQ ID NO:12), peptide 2: AA 277-286 PGFGDNRKNQ (SEQ ID NO:13), and peptide (AA) 516-528: KGIIDPTKWRTA (SEQ ID NO:14); and
a third species of epitope capable of eliciting an anti-arteriosclerotic vascular disease response via a third pathway that is independent from the first pathway and is independently selected from the group consisting of a PAR-1 epitope or a *Mycobacterium bovis* HSP epitope.

14. The construct according to claim 1, wherein the epitopes portion of the construct comprises RPHC wherein R is SEQ ID NO: 9, P is SEQ ID NO: 19, H is SEQ ID NO: 12 and C is a combination of amino acid 66-73 (SEQ ID NO: 16) from major outer membrane protein (MOMP) and amino acid 283-291 (SEQ ID NO: 17) from outer membrane protein 5 of *Chlamydia pneumoniae*.

15. The construct according to claim 1, wherein the PAR-1 epitope comprises an amino acid selected from the group consisting of EWEPKPVNQVYT (SEQ ID NO:18) and SFLLRNPNDKYEPF (SEQ ID NO:19).

16. The construct according to claim 1, wherein the *Mycobacterium bovis* HSP epitope is mycobacterium (AA) 253-268: EGEALSTLVVNKIRGT (SEQ ID NO:15).

* * * * *

SEQUENCE LISTING

```
<160> NUMBER OF SEQ ID NOS: 19

<210> SEQ ID NO 1
<211> LENGTH: 59
<212> TYPE: PRT
<213> ORGANISM: Artificial Sequence
<220> FEATURE:
<223> OTHER INFORMATION: modified neurotoxin

<400> SEQUENCE: 1
```

```
Arg Ile Cys Tyr Asn His Leu Gly Thr Lys Pro Pro Thr Thr Glu Thr
 1               5                  10                  15

Cys Gln Glu Asp Ser Cys Tyr Lys Asn Ile Trp Thr Phe Asp Asn Ile
            20                  25                  30

Ile Arg Arg Gly Cys Gly Cys Phe Thr Pro Arg Gly Asp Met Pro Gly
        35                  40                  45

Pro Tyr Cys Cys Glu Ser Asp Lys Cys Asn Leu
    50                  55
```

<210> SEQ ID NO 2
<211> LENGTH: 74
<212> TYPE: PRT
<213> ORGANISM: Homo sapiens

<400> SEQUENCE: 2

```
Thr Leu Gln Lys Lys Ile Glu Glu Ile Ala Ala Lys Tyr Lys His Ser
 1               5                  10                  15

Val Val Lys Lys Cys Cys Tyr Asp Gly Ala Cys Val Asn Asn Asp Glu
            20                  25                  30

Thr Cys Glu Gln Arg Ala Ala Arg Ile Ser Leu Gly Pro Arg Cys Ile
        35                  40                  45

Lys Ala Phe Thr Glu Cys Cys Val Val Ala Ser Gln Leu Arg Ala Asn
    50                  55                  60

Ile Ser His Lys Asp Met Gln Leu Gly Arg
65                  70
```

<210> SEQ ID NO 3
<211> LENGTH: 12
<212> TYPE: PRT
<213> ORGANISM: Homo sapiens

<400> SEQUENCE: 3

```
Glu Gln Arg Ala Ala Arg Ile Ser Leu Gly Pro Arg
 1               5                  10
```

<210> SEQ ID NO 4
<211> LENGTH: 17
<212> TYPE: PRT
<213> ORGANISM: Homo sapiens

<400> SEQUENCE: 4

```
Arg Ala Ala Arg Ile Ser Leu Gly Pro Arg Cys Ile Lys Ala Phe Thr
 1               5                  10                  15

Glu
```

<210> SEQ ID NO 5
<211> LENGTH: 10
<212> TYPE: PRT
<213> ORGANISM: Homo sapiens

<400> SEQUENCE: 5

```
Cys Val Asn Asn Asp Glu Thr Cys Glu Gln
 1               5                  10
```

<210> SEQ ID NO 6
<211> LENGTH: 350
<212> TYPE: PRT
<213> ORGANISM: Homo sapiens

<400> SEQUENCE: 6

```
Met Asn Ser Phe Asn Tyr Thr Thr Pro Asp Tyr Gly His Tyr Asp Asp
```

-continued

```
1               5                   10                  15
Lys Asp Thr Leu Asp Leu Asn Thr Pro Val Asp Lys Thr Ser Asn Thr
            20                  25                  30

Leu Arg Val Pro Asp Ile Leu Ala Leu Val Ile Phe Ala Val Val Phe
            35                  40                  45

Leu Val Gly Val Leu Gly Asn Ala Leu Val Val Trp Val Thr Ala Phe
 50                      55                  60

Glu Ala Lys Arg Thr Ile Asn Ala Ile Trp Phe Leu Asn Leu Ala Val
 65                  70                  75                  80

Ala Asp Phe Leu Ser Cys Leu Ala Leu Pro Ile Leu Phe Thr Ser Ile
                85                  90                  95

Val Gln His His His Trp Pro Phe Gly Gly Ala Ala Cys Ser Ile Leu
                100                 105                 110

Pro Ser Leu Ile Leu Leu Asn Met Tyr Ala Ser Ile Leu Leu Leu Ala
            115                 120                 125

Thr Ile Ser Ala Asp Arg Phe Leu Leu Val Phe Lys Pro Ile Trp Cys
 130                 135                 140

Gln Asn Phe Arg Gly Ala Gly Leu Ala Trp Ile Ala Cys Ala Val Ala
145                 150                 155                 160

Trp Gly Leu Ala Leu Leu Leu Thr Ile Pro Ser Phe Leu Tyr Arg Val
                165                 170                 175

Val Arg Glu Glu Tyr Phe Pro Pro Lys Val Leu Cys Gly Val Asp Tyr
                180                 185                 190

Ser His Asp Lys Arg Arg Glu Arg Ala Val Ala Ile Val Arg Leu Val
            195                 200                 205

Leu Gly Phe Leu Trp Pro Leu Leu Thr Leu Thr Ile Cys Tyr Thr Phe
 210                 215                 220

Ile Leu Leu Arg Thr Trp Ser Arg Arg Ala Thr Arg Ser Thr Lys Thr
225                 230                 235                 240

Leu Lys Val Val Val Ala Val Val Ala Ser Phe Phe Ile Phe Trp Leu
                245                 250                 255

Pro Tyr Gln Val Thr Gly Ile Met Met Ser Phe Leu Glu Pro Ser Ser
                260                 265                 270

Pro Thr Phe Leu Leu Leu Asn Lys Leu Asp Ser Leu Cys Val Ser Phe
            275                 280                 285

Ala Tyr Ile Asn Cys Cys Ile Asn Pro Ile Ile Tyr Val Val Ala Gly
            290                 295                 300

Gln Gly Phe Gln Gly Arg Leu Arg Lys Ser Leu Pro Ser Leu Leu Arg
305                 310                 315                 320

Asn Val Leu Thr Glu Glu Ser Val Val Arg Glu Ser Lys Ser Phe Thr
                325                 330                 335

Arg Ser Thr Val Asp Thr Met Ala Gln Lys Thr Gln Ala Val
                340                 345                 350

<210> SEQ ID NO 7
<211> LENGTH: 21
<212> TYPE: PRT
<213> ORGANISM: Homo sapiens

<400> SEQUENCE: 7

Met Asn Ser Phe Asn Tyr Thr Thr Pro Asp Tyr Gly His Tyr Asp Asp
 1               5                   10                  15

Lys Asp Thr Leu Asp
            20
```

```
<210> SEQ ID NO 8
<211> LENGTH: 13
<212> TYPE: PRT
<213> ORGANISM: Homo sapiens

<400> SEQUENCE: 8

Thr Leu Asp Leu Asn Thr Pro Val Asp Lys Thr Ser Asn
1               5                   10

<210> SEQ ID NO 9
<211> LENGTH: 31
<212> TYPE: PRT
<213> ORGANISM: Homo sapiens

<400> SEQUENCE: 9

Met Asn Ser Phe Asn Tyr Thr Thr Pro Asp Tyr Gly His Tyr Asp Asp
1               5                   10                  15

Lys Asp Thr Leu Asp Leu Asn Thr Pro Val Asp Lys Thr Ser Asn
            20                  25                  30

<210> SEQ ID NO 10
<211> LENGTH: 8
<212> TYPE: PRT
<213> ORGANISM: Homo sapiens

<400> SEQUENCE: 10

Ala Glu Leu Lys Lys Gln Ser Lys
1               5

<210> SEQ ID NO 11
<211> LENGTH: 11
<212> TYPE: PRT
<213> ORGANISM: Homo sapiens

<400> SEQUENCE: 11

Ala Glu Leu Lys Lys Gln Ser Lys Pro Val Thr
1               5                   10

<210> SEQ ID NO 12
<211> LENGTH: 10
<212> TYPE: PRT
<213> ORGANISM: Homo sapiens

<400> SEQUENCE: 12

Pro Gly Phe Gly Asp Asn Arg Lys Asn Gln
1               5                   10

<210> SEQ ID NO 13
<211> LENGTH: 10
<212> TYPE: PRT
<213> ORGANISM: Homo sapiens

<400> SEQUENCE: 13

Pro Gly Phe Gly Asp Asn Arg Lys Asn Gln
1               5                   10

<210> SEQ ID NO 14
<211> LENGTH: 13
<212> TYPE: PRT
<213> ORGANISM: Homo sapiens

<400> SEQUENCE: 14

Lys Gly Ile Ile Asp Pro Thr Lys Val Val Arg Thr Ala
1               5                   10
```

```
<210> SEQ ID NO 15
<211> LENGTH: 16
<212> TYPE: PRT
<213> ORGANISM: Mycobacterium africanum

<400> SEQUENCE: 15

Glu Gly Glu Ala Leu Ser Thr Leu Val Val Asn Lys Ile Arg Gly Thr
1               5                   10                  15

<210> SEQ ID NO 16
<211> LENGTH: 8
<212> TYPE: PRT
<213> ORGANISM: Chlamydia pneumoniae

<400> SEQUENCE: 16

Gly Asp Tyr Val Phe Asp Arg Ile
1               5

<210> SEQ ID NO 17
<211> LENGTH: 9
<212> TYPE: PRT
<213> ORGANISM: Chlamydia pneumoniae

<400> SEQUENCE: 17

Gln Ala Val Ala Asn Gly Gly Ala Ile
1               5

<210> SEQ ID NO 18
<211> LENGTH: 12
<212> TYPE: PRT
<213> ORGANISM: Homo sapiens

<400> SEQUENCE: 18

Glu Trp Glu Pro Lys Pro Val Asn Gln Val Tyr Thr
1               5                   10

<210> SEQ ID NO 19
<211> LENGTH: 14
<212> TYPE: PRT
<213> ORGANISM: Homo sapiens

<400> SEQUENCE: 19

Ser Phe Leu Leu Arg Asn Pro Asn Asp Lys Tyr Glu Pro Phe
1               5                   10
```